(12) United States Patent
Kovarik

(10) Patent No.: US 11,529,412 B2
(45) Date of Patent: Dec. 20, 2022

(54) METHOD AND SYSTEM FOR PROTECTING HONEY BEES FROM PESTICIDES

(71) Applicant: Joseph E. Kovarik, Englewood, CO (US)

(72) Inventor: Joseph E. Kovarik, Englewood, CO (US)

(73) Assignee: Seed Health, Inc., Venice (CA)

( * ) Notice: Subject to any disclaimer, the term of this patent is extended or adjusted under 35 U.S.C. 154(b) by 29 days.

(21) Appl. No.: 17/185,618

(22) Filed: Feb. 25, 2021

(65) Prior Publication Data

US 2021/0177963 A1   Jun. 17, 2021

Related U.S. Application Data

(63) Continuation-in-part of application No. 16/892,623, filed on Jun. 4, 2020, now Pat. No. 10,933,128, which is a continuation-in-part of application No. 16/246,652, filed on Jan. 14, 2019, now Pat. No. 10,675,347, which is a continuation-in-part of application No. 16/139,232, filed on Sep. 24, 2018, now Pat. No. 10,568,916, which is a continuation-in-part of application No. 15/379,579, filed on Dec. 15, 2016, now Pat. No. 10,086,024, said application No. 17/185,618 is a continuation-in-part of application No. 15/270,034, filed on Sep. 20, 2016, now Pat. No. 9,750,802, which is a continuation of application No. 14/954,074, filed on Nov. 30, 2015, now Pat. No. 9,457,077.

(60) Provisional application No. 62/277,571, filed on Jan. 12, 2016, provisional application No. 62/278,046, filed on Jan. 13, 2016.

(51) Int. Cl.
| | | |
|---|---|---|
| *A61K 39/35* | (2006.01) | |
| *A61K 35/742* | (2015.01) | |
| *A61K 9/00* | (2006.01) | |
| *A61K 45/06* | (2006.01) | |
| *A61K 39/395* | (2006.01) | |
| *A61K 35/745* | (2015.01) | |
| *C07K 16/00* | (2006.01) | |
| *A61K 39/39* | (2006.01) | |
| *A61K 35/747* | (2015.01) | |
| *A61K 35/74* | (2015.01) | |
| *A61K 39/00* | (2006.01) | |
| *A61K 35/741* | (2015.01) | |

(52) U.S. Cl.
CPC .............. *A61K 39/35* (2013.01); *A61K 9/007* (2013.01); *A61K 9/0034* (2013.01); *A61K 9/0043* (2013.01); *A61K 35/74* (2013.01); *A61K 35/741* (2013.01); *A61K 35/742* (2013.01); *A61K 35/745* (2013.01); *A61K 35/747* (2013.01); *A61K 39/0008* (2013.01); *A61K 39/39* (2013.01); *A61K 39/395* (2013.01); *A61K 45/06* (2013.01); *C07K 16/00* (2013.01); *A61K 2039/505* (2013.01); *A61K 2039/541* (2013.01); *A61K 2039/544* (2013.01); *A61K 2039/55* (2013.01); *A61K 2039/55583* (2013.01); *A61K 2039/577* (2013.01); *A61K 2039/58* (2013.01); *A61K 2039/70* (2013.01)

(58) Field of Classification Search
None
See application file for complete search history.

(56) References Cited

U.S. PATENT DOCUMENTS

| | | |
|---|---|---|
| 3,178,341 A | 4/1965 | Hamill et al. |
| 4,687,841 A | 8/1987 | Spilburg et al. |
| 4,720,486 A | 1/1988 | Spilburg et al. |
| 6,287,610 B1 | 9/2001 | Bowling et al. |
| 6,569,474 B2 | 5/2003 | Clayton et al. |
| 7,267,975 B2 | 9/2007 | Strobel et al. |
| 7,820,420 B2 | 10/2010 | Whitlock |
| 7,846,711 B2 | 12/2010 | Boettner et al. |
| 8,349,313 B2 | 1/2013 | Smith et al. |
| 8,481,299 B2 | 7/2013 | Gueniche |
| 8,496,914 B2 | 7/2013 | Bonfiglio |
| 8,585,588 B2 | 11/2013 | Kovarik et al. |
| 8,685,389 B2 | 4/2014 | Baur |
| 8,701,671 B2 | 4/2014 | Kovarik |
| 8,758,764 B2 | 6/2014 | Masignani et al. |
| 8,815,538 B2 | 8/2014 | Lanzalaco et al. |
| 8,951,775 B2 | 2/2015 | Castiel |
| 9,011,834 B1 | 4/2015 | McKenzie et al. |
| 9,028,841 B2 | 5/2015 | Henn et al. |
| 9,131,884 B2 | 9/2015 | Holmes |
| 9,234,204 B2 | 1/2016 | Qvit-Raz et al. |
| 9,288,981 B2 | 3/2016 | Gandhi et al. |
| 10,086,024 B2 | 10/2018 | Kovarik |
| 10,675,347 B2 | 6/2020 | Kovarik |

(Continued)

FOREIGN PATENT DOCUMENTS

| | | |
|---|---|---|
| WO | WO-2011138310 A2 | 11/2011 |
| WO | WO-2017/040343 | 3/2017 |

OTHER PUBLICATIONS

Daisley et al. The ISME Journal 14:476-491, 2020 (published online Oct. 29, 2019).*

(Continued)

*Primary Examiner* — Oluwatosin A Ogunbiyi
(74) *Attorney, Agent, or Firm* — Sheridan Ross P.C.

(57) ABSTRACT

A method and system for the treatment of honey bees (*Apis mellifera*), bats, and butterflies protects them from various life threatening conditions, including Colony Collapse Disorder and in particular, provides honey bees with the ability to assimilate and degrade pesticides such as neonicotinoids and fipronil.

19 Claims, 3 Drawing Sheets

(56) References Cited

U.S. PATENT DOCUMENTS

Figure 1:
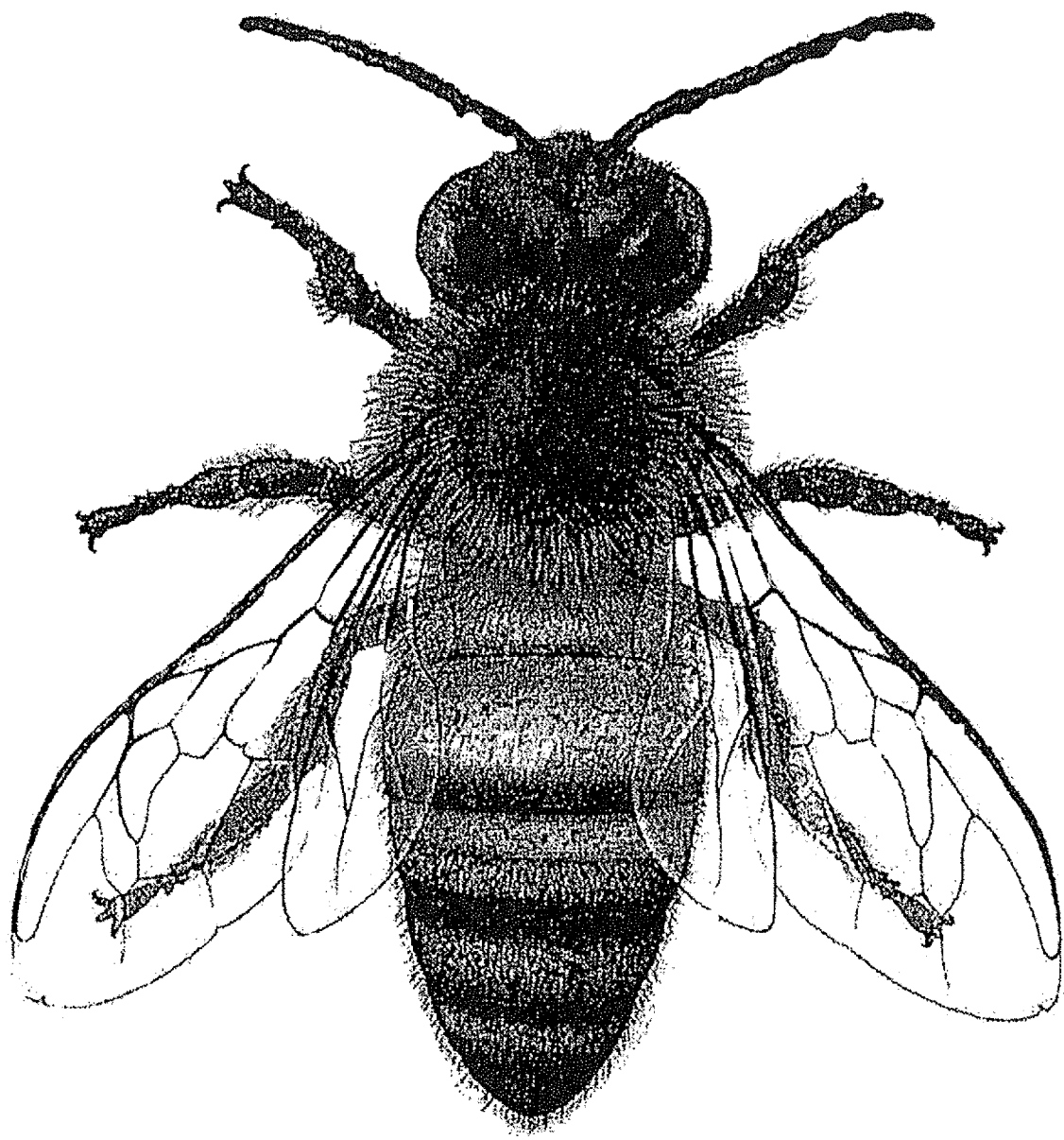
Figure 2:
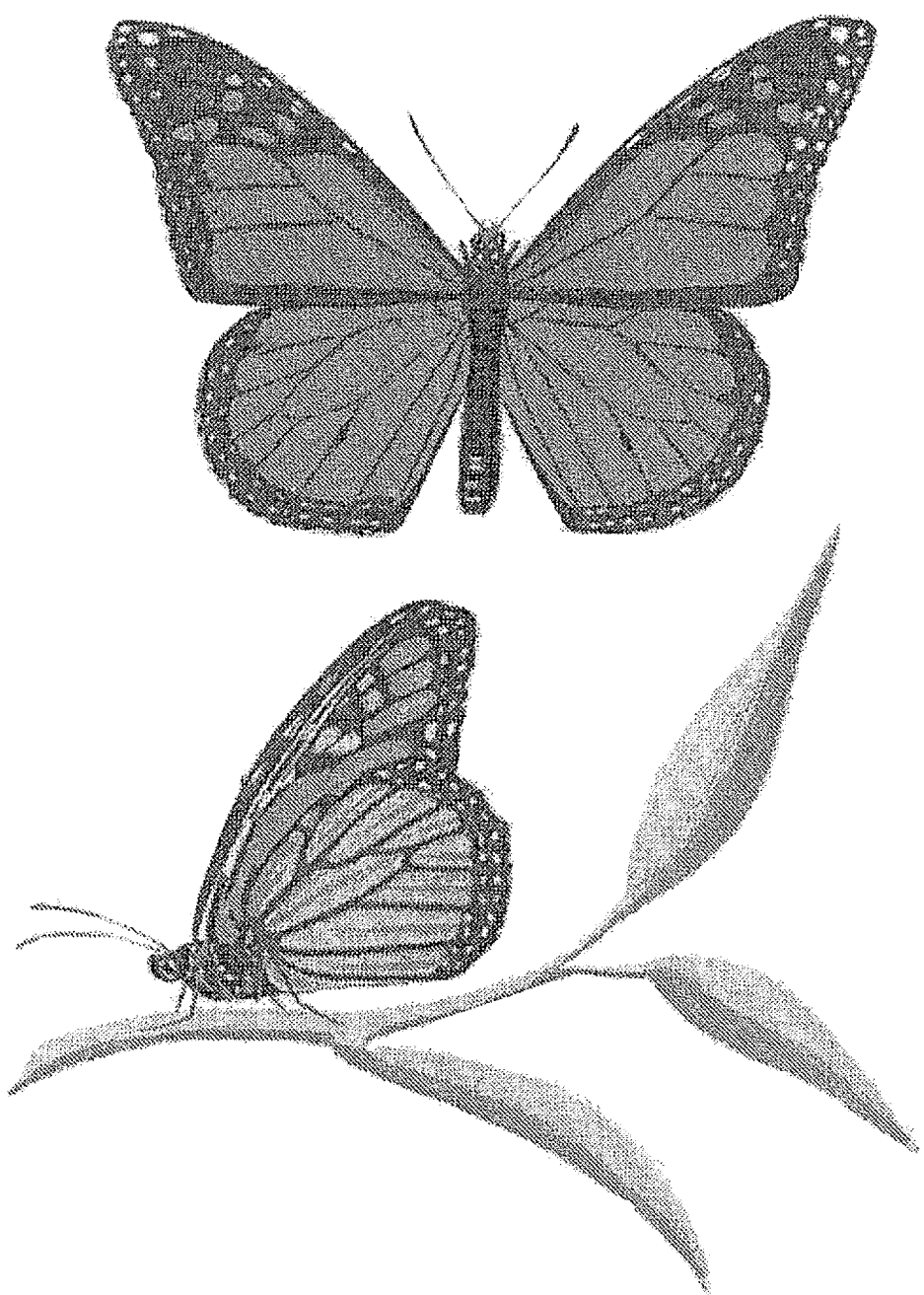
Figure 3:
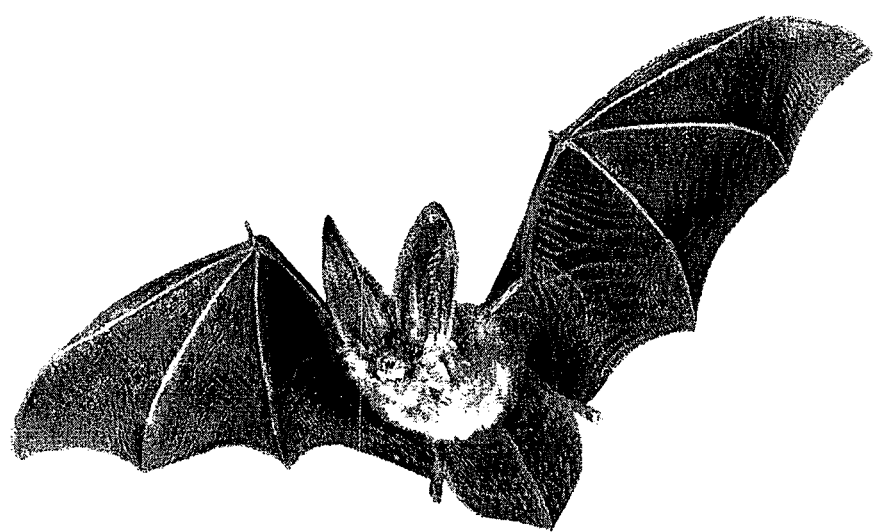

| | | |
|---|---|---|
| 10,933,128 B2 | 3/2021 | Kovarik |
| 2002/0009436 A1 | 1/2002 | Doyle et al. |
| 2003/0206995 A1 | 11/2003 | Bowling et al. |
| 2007/0054008 A1 | 3/2007 | Clayton et al. |
| 2007/0207955 A1 | 9/2007 | Tanihara et al. |
| 2009/0205083 A1 | 8/2009 | Gupta et al. |
| 2010/0029832 A1 | 2/2010 | Pinnavaia et al. |
| 2012/0027786 A1 | 2/2012 | Gupta |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0064796 A1 | 3/2013 | Hamdi |
| 2013/0157876 A1 | 6/2013 | Lynch et al. |
| 2013/0259834 A1 | 10/2013 | Klaenhammer et al. |
| 2013/0315869 A1 | 11/2013 | Qimron et al. |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0068797 A1 | 3/2014 | Doudna et al. |
| 2014/0154290 A1 | 6/2014 | Peters et al. |
| 2014/0212520 A1 | 7/2014 | Del Vecchio et al. |
| 2014/0255351 A1 | 9/2014 | Berstad et al. |
| 2014/0349405 A1 | 11/2014 | Sontheimer et al. |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0166641 A1 | 6/2015 | Goodman |
| 2015/0190435 A1 | 7/2015 | Henn et al. |
| 2015/0216917 A1 | 8/2015 | Jones |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0024510 A1 | 1/2016 | Bikard et al. |
| 2016/0040216 A1 | 2/2016 | Wilder |
| 2016/0089315 A1 | 3/2016 | Kleinberg et al. |
| 2016/0151427 A1 | 6/2016 | Whitlock et al. |
| 2016/0168594 A1 | 6/2016 | Zhang et al. |
| 2016/0206668 A1 | 7/2016 | Kort et al. |
| 2016/0271106 A1 | 9/2016 | Shi et al. |
| 2016/0271189 A1 | 9/2016 | Cutcliffe |
| 2016/0314281 A1 | 10/2016 | Apte |
| 2016/0354416 A1 | 12/2016 | Gajewski et al. |
| 2017/0020932 A1 | 1/2017 | Cutcliffe et al. |
| 2017/0021011 A1 | 1/2017 | Kovarik et al. |
| 2017/0035820 A1 | 2/2017 | Stamets et al. |
| 2017/0071986 A1 | 3/2017 | Kovarik et al. |
| 2018/0020678 A1 | 1/2018 | Scharf et al. |
| 2018/0119132 A1 | 5/2018 | Hutchinson et al. |
| 2018/0177160 A1 | 6/2018 | Wagoner et al. |
| 2018/0216123 A1 | 8/2018 | Anand et al. |
| 2019/0015528 A1 | 1/2019 | Moran et al. |
| 2019/0022151 A1 | 1/2019 | Kovarik |
| 2019/0177807 A1 | 6/2019 | Wan et al. |
| 2019/0321417 A1 | 10/2019 | Brucker et al. |
| 2020/0318139 A1 | 10/2020 | Gersbach et al. |

OTHER PUBLICATIONS

Chmiel et al. Frontiers in Ecology and Evolution, vol. 8, article 22, pp. 1-19, Feb. 19, 2020.*

Team British Columbia, Probeeotics UBC Igem 2015, pp. 1-46.

Team British Columbia, Welcome to the UBC Igem Wiki, pp. 1-4, http://2015.igem.org/Team: British_Columbia.

Zhai, et al., Molecular cloning, purification and biochemical characterization of a novel pyrethroid-hydrolyzing carboxyl esterase gene from *Ochrobactrum anthropi* YZ-1, Journal of Hazardous Materials, Jun. 2012, pp. 206-212.

P.C. Wu, Y.H. Liu, Z.Y. Wang, X.Y. Zhang, H. Li, W.Q. Liang, N. Luo, J.M. Hu, J.Q. Lu, T.G. Luan, L.X. Cao Molecular cloning, purification, and biochemical characterization of a novel pyrethroid-hydrolyzing esterase from *Klebsiella* sp. strain ZD112, J. Agric. Food Chem., 54 (2006), pp. 836-842.

B.Z. Wang, p. Guo, B.J. Hang, L. Li, J. He, S.P. Li Cloning of a novel pyrethroid-hydrolyzing carboxylesterase gene from *Sphingobium* sp. JZ-1 and characterization of the gene product; Appl. Environ. Microbiol., 75 (2009), pp. 5496-5500.

G. Li, K. Wang, Y.H. Liu Molecular cloning and characterization of a novel pyrethroid-hydrolyzing esterase originating from the metagenome; Microb. Cell Factories, 7 (2008).

S Pankaj, S Gangola, P Khati, G Kumar, A Srivastava—Novel pathway of cypermethrin biodegradation in a *Bacillus* sp. strain SG2 isolated from cypermethrin-contaminated agriculture field; 3 Biotech, 2016—ncbi.nlm.nih.gov.

H Itoh, K Tago, M Hayatsu, Y Kikuchi—Natural product reports, 2018; Detoxifying symbiosis: microbe-mediated detoxification of phytotoxins and pesticides in insects;—pubs.rsc.org.

T Gong, X Xu, Y Dang, A Kong, Y Wu, P Liang . . . An engineered *Pseudomonas putida* can simultaneously degrade organophosphates, pyrethroids and carbamates—Science of The Total . . . , 2018—Elsevier.

Smith et al., bioRxiv preprint (Jul. 11, 2018), Genomic signatures of honey bee association in an acetic acid symbiont.

Huang et al., Genome Sequencing and Comparative Analysis of Stenotrophomonas acidaminiphila, Reveal Evolutionary Insights Into Sulfamethoxazole Resistance, Front Microbiol. 2018; 9: 1013.

Degradation of fipronil by Stenotrophomonasacidaminiphila, Uniyal, et. al, Degradation of fipronil by Stenotrophomonasacidaminiphila isolated from rhizospheric soil of *Zea mays*, 3 Biotech. Jun. 2016; 6(1): 48.

Mandal K, et. al, Microbial degradation of fipronil by Bacillus thuringiensis, Ecotoxicol Environ Saf. Jul. 2013; 93:87-92.

Medhi, et. al, Genome Sequence of a Heterotrophic Nitrifierand Aerobic Denitrifier, *Paracoccus denitrificans* Strain ISTOD1, Isolated from Wastewater, Genome Announc. Apr. 2018; 6(15): e00210-18.

Kumar et al., Biodegradation of Fipronil by *Paracoccus* sp in Different Types of Soil, Bulletin of Environmental Contamination and Toxicology 88(5):781-7 (2012).

CRISPR/Cas9 & Targeted Genome Editing: New Era in Molecular Biology https://www.neb.com/tools-and-resources/feature-articles/crispr-case9-and-targeted-genome-editing-a-new-era-in-molecular-biology retrieved Aug. 22, 2019.

* cited by examiner

METHOD AND SYSTEM FOR PROTECTING HONEY BEES FROM PESTICIDES

RELATED APPLICATIONS

This application is a continuation-in-part of U.S. patent application Ser. No. 16/892,623, filed Jun. 4, 2020 (now U.S. Pat. No. 10,933,128, issued Mar. 2, 2021), which is a continuation-in-part of U.S. patent application Ser. No. 16/246,652, filed Jan. 14, 2019 (now U.S. Pat. No. 10,675,347, issued Jun. 9, 2020), which is a continuation-in-part application of U.S. patent application Ser. No. 16/139,232, filed Sep. 24, 2018 (now U.S. Pat. No. 10,568,916, issued Feb. 25, 2020), which is a continuation-in-part application of U.S. patent application Ser. No. 15/379,579, filed Dec. 15, 2016 (now U.S. patent Ser. No. 10/086,024, issued Oct. 2, 2018), which claims priority from U.S. Provisional Patent Application Ser. No. 62/277,568, filed on Jan. 12, 2016, from U.S. Provisional Patent Application Ser. No. 62/277,571, filed on Jan. 12, 2016 and U.S. Provisional Patent Application Ser. No. 62/278,046, filed on Jan. 13, 2016.

This application also is a continuation-in-part of U.S. patent application Ser. No. 15/270,034, filed on Sep. 20, 2016 (now U.S. Pat. No. 9,750,802, issued Sep. 5, 2017, which is a continuation of U.S. patent application Ser. No. 14/954,074, filed on Nov. 30, 2015 (now U.S. Pat. No. 9,457,077, issued Oct. 4, 2016).

The entire disclosure of the prior applications are considered to be part of the disclosure of the accompanying application and are hereby incorporated by reference.

FIELD OF THE INVENTION

The present invention relates to a method and system for the treatment of honey bees (*Apis mellifera*), bats, and butterflies to protect them from various life threatening conditions, including Colony Collapse Disorder, white nose syndrome, etc. and in particular, is directed to providing honey bees, bats and butterflies with the ability to assimilate and degrade neonicotinoids.

BACKGROUND OF THE INVENTION

Pollinating insects are key to the evolutionary and ecological success of flowering plants and enable much of the diversity in the human diet. Bees are arguably one of the most important beneficial insects worldwide. Their positive impact can be measured by the value they contribute to the agricultural economy, their ecological role in providing pollination services, and the hive products they produce. The honey bee is credited with approximately 85% of the pollinating activity necessary to supply about one-quarter to one-third of the nation's food supply. Over 50 major crops in the United States either depend on honey bees for pollination or produce more abundantly when honey bees are plentiful.

Approximately 90% of flowering plants—corresponding to nearly three quarters of global agricultural crops—use pollinators to set seed and fruit. Populations of several species of pollinators, however, are in decline throughout the world, threatening the stability of our ecosystems and productivity of our agricultural landscapes.

Bees are vital to global biodiversity and food security through their pollination of plants, including several key crops. Honey bees, however, are exposed to myriad of stressors including pests, pathogens, pesticides, poor nutrition due to monocropping and habitat loss leading to extreme colony losses.

In about 2006-2007, the discovery of the devastating effects of Colony Collapse Disorder on U.S. honey bee populations was first noticed. Overwhelming evidence now suggests that numerous wild and managed bee populations are in decline. This has led to concerns over human food security and maintenance of biodiversity. Recent losses of honeybee colonies have been linked to several non-exclusive factors; such as pests, parasites, pesticides (e.g., neonicotinoids) and other toxins. In the last 20 years, the bee-keeping sector registered very consistent losses worldwide, in terms of bee numbers and productivity. Queen health is crucial to colony survival of social bees. Recently, queen failure has been proposed to be a major driver of managed honey bee colony losses. The role of queens (primary reproductive females that can produce diploid offspring) in social bee colony survival is indispensable. There have been anecdotal reports of 'poor quality queens' (i.e. queen failure) of the western honey bee (*Apis mellifera*; hereafter honey bee), throughout the northern hemisphere.

Common microbial pathogens appear to be major threats to honey bees, while sublethal doses of pesticide may enhance their deleterious effects on honey bee larvae and adults. Honey bees are suffering from elevated colony losses in the northern hemisphere possibly because of a variety of emergent microbial pathogens, with which pesticides may interact to exacerbate their impacts.

More than six decades after the onset of wide-scale commercial use of synthetic pesticides and more than fifty years after Rachel Carson's Silent Spring, pesticides, particularly insecticides, arguably remain the most influential pest management tool around the globe. Nevertheless, pesticide use is still a controversial issue and is at the regulatory forefront in most countries. Neonicotinoids are suspected to pose an unacceptable risk to bees, partly because of their systemic uptake in plants. The European Union has therefore introduced a moratorium on three neonicotinoids as seed coatings in flowering crops that attract bees. The neonicotinoid class of chemical pesticides has recently received considerable attention because of potential risks it poses to ecosystem functioning and services. Ubiquitously used for management of harmful insects in the last decade, these systemic chemicals persist in the environment, thereby promoting their contact with non-target organisms such as pollinating bees.

Sub-lethal doses of neonicotinoids have been shown to negatively impact the health of honeybees. Understanding the effects of neonicotinoid insecticides on bees is vital because of reported declines in bee diversity and distribution and the crucial role bees have as pollinators in ecosystems and agriculture. Pollinators perform sophisticated behaviors' while foraging that require them to learn and remember floral traits associated with food. Neonicotinoid pesticides, at levels shown to occur in the wild, interfere with the learning circuits in the bee's brain. Pesticides have a direct impact on pollinator brain physiology. Disruption in this important function has profound implications for honeybee colony survival, because bees that cannot learn will not be able to find food. Both honey bees and bumble bees prefer sugar solutions laced with the neonicotinoids imidacloprid, clothianidin, and thiamethoxam over pure sugar water, presumably due to the nicotine-like addition that is so common in humans.

On Apr. 2, 2015, the EPA announced that it will not be approving new outdoor uses of neonicotinoids until pollinator risk assessments are complete. Tests include acute and chronic toxicity tests for adults and larvae, field feeding studies, foliage toxicity, residues in pollen and nectar, and realistic field experiments that look at long term effects.

Canola is becoming a favored crop in the prairies, with over a million acres (1700 square miles) to be planted in North Dakota alone this year. Bayer CropScience grows hybrid canola seed in Canada, and in an ironic twist, is thereby the largest renter of honey bee pollination services in Canada, and is thus highly motivated to ensure that the product does not harm bees. Virtually all canola seed is treated with clothianidin or its precursor, thiamethoxam.

There is therefore a long felt but unsolved need for a system and method to protect honey bees from the increasing use of neonicotinoid insecticides which are believed to be at least partially responsible for the recent demise of honey bee populations.

The corpses of hibernating bats were first found blanketing caves in the northeastern United States in 2006. The disease that killed them, caused by a cold-loving fungus called *Geomyces destructans*—and dubbed White-nose Syndrome (WNS) for the tell-tale white fuzz it leaves on bats' ears and noses—has since destroyed at least one million Bats, becoming one of the most precipitous wildlife decline in the past century in North America. WNS is a fungal disease that has its greatest impacts during bat hibernation and emergence. Bats in torpor experience reduced immune function, thus potentially compromising their ability to combat WNS. Fat reserves are metabolized during hibernation, a process that can mobilize contaminants to the brain and other tissues coincident with reduced immune function. CECs, such as PBDEs, bisphenol A, and triclosan, may further diminish immune competence.

Bats are especially vulnerable to chemical pollution. They're small—the little brown bat weighs just 8 grams—and can live for up to three decades. For their body size, bats live longer than any other order of mammal. Bats may be more susceptible than other mammals to the effects of low doses of bioaccumulative contaminants due to their annual life cycles, requiring significant fat deposition followed by extreme fat depletion during hibernation or migration, at which time contaminants may be mobilized into the brain and other tissues.

There is a growing body of science directly implicating neonicotinoid (neonic) pesticides in the significant decline of bees and other pollinators, including bats. Pollinator decline has been found on every continent in the world, and hundreds of pollinator species are on the verge of extinction. Since 2006, bees in the U.S. have been dying off or seemingly abandoning their hives—a phenomenon known as Colony Collapse Disorder. While there are many contributors to pollinator decline, two of the most important are the loss of habitat and the introduction and expansion of use of new pesticides on agricultural cropland. A specific concern centers on neonicotinoids, a relatively new class of systemic insecticides, often applied as a seed coating in commodity agriculture.

Neonicotinoids came into wide use in the early 2000s. Unlike older pesticides that evaporate or disperse shortly after application, neonicotinoids are systemic poisons. Applied to the soil or doused on seeds, neonicotinoid insecticides incorporate themselves into plant tissues, turning the plant itself into a tiny poison factory emitting toxin from its roots, leaves, stems, pollen, and nectar. As the name suggest, neonicotinoids are similar in structure to nicotine and paralyze or disorient insects by blocking a pathway that transmits nerve impulses in the insect's central nervous system.

Neonicotinoids are used to control a wide variety of insects. The first neonicotinoid, imidacloprid (Admire), became available in the United States in 1994 and is currently present in over 400 products on the market. Other neonic insecticides include acetamiprid, clothianidin, dinotefuran, nitenpyram, thiacloprid, and thiamethoxam. In 2006, neonicotinoids accounted for over 17 percent of the global insecticide market. Two of them—clothianidin and thiamethoxam—dominate the global market for insecticidal seed treatments and are used to coat the seeds of most of the annual crops planted around the world. In fact, more than 94 percent of the corn and more than 30 percent of the soy planted in the United States is pretreated with neonicotinoids.

The introduction of neonicotinoids into the agricultural marketplace occurred around the same time as the introduction of GMO crops in the mid-to-late 1990s. Monsanto and Syngenta, the undisputed leaders in patented genetically engineered seeds, also have close relationships with the leading global neonic producer, Bayer. Most new commodity crops are increasingly coming to farmers with stacked traits, which means more than one transgenic alteration. These genetically engineered and transplanted traits are marketed to farmers as providing benefits such as resistance to multiple herbicides, pests, funguses, heat and drought.

Seed treatment applications are prophylactic, meaning they are used whether or not there is any evidence of pest pressures. At least 30 percent of soybean seeds planted annually (approximately 22.5 million out of 75 million acres) are pretreated with neonic insecticides (two of the primary four being imidacloprid and thiamethoxam). But corn has the highest use and acreage with around 94 percent of U.S. corn treated with a neonicotinoid. That widespread use has quickly elevated the Midwest to the highest levels of neonicotinoid use in the country. These neonicotinoids don't stay in the plants and soil however, but find their ways into the water as well. A recent U.S. Geological Survey report confirmed that neonicotinoids were common in streams throughout the Midwest. Bats frequently forage in aquatic and terrestrial habitats that may be subjected to discharges from wastewater treatment plants, agricultural operations, and other point and nonpoint sources of contaminants.

Death is not the only outcome of pesticide exposure. Sub-lethal doses of neonicotinoids can disrupt pollinators' cognitive abilities, communication and physiology. Neonicotinoids also have harmful synergistic impacts on pollinators in combination with other chemicals in the field, compounding their effects. Scientists have shown in multiple studies that the combined presence of neonicotinoids and some fungicides can increase the potency of neonicotinoids by more than 1,000-fold. In addition to their toxicity, neonicotinoids persist in plants much longer than most other insecticides, thereby compounding their impact on pollinators. They can reside in plant tissues for over a year, and some can persist for even longer in the soil. This means pollinators and other animals are exposed to the chemicals for extended periods of time and in some regions year-round.

There is a desperate need for an effective treatment to advert the destruction of bat species that has been observed over the last decade. The ramifications of the elimination of such an important pollinator, such as the bat, will have tremendous and as yet unforeseen negative effects on the environment. A need for a treatment is therefore long felt and unsolved. The present invention is directed to a method and system that achieves this objective.

The annual migration of North America's monarch butterfly (*Danaus plexippus* Kluk (Lepidoptera: Nymphalidae)) is a unique and amazing phenomenon. The monarch is the only butterfly known to make a two-way migration as birds do. Unlike other butterflies that can overwinter as larvae, pupae, or even as adults in some species, monarchs cannot survive the cold winters of northern climates. Using environmental cues, the monarchs know when it is time to travel south for the winter. Monarchs use a combination of air currents and thermals to travel long distances. Some fly as far as 3,000 miles to reach their winter home. The multi-generational migration of North American monarch butterflies between breeding grounds in the northern U.S. and southern Canada and wintering grounds in central Mexico and coastal California is one of the world's most spectacular natural events. The interest in monarchs and their fascinating, visible biology is demonstrated by monarch butterflies being the official insect or butterfly of seven U.S. states; celebrated via festivals in Mexico, the United States, and Canada; the focus of science curricula; and the subject of multiple citizen-science projects.

Monarch butterfly populations have declined precipitously in North America in the last twenty years. This decline has commonly been linked to loss of milkweeds (*Asclepias* species) from farmer's fields. Monarch caterpillars are dependent on milkweeds. The ability of farmers to kill them with the Monsanto herbicide Roundup (glyphosate) has therefore led to this herbicide being considered as a major contributor to the decline of the monarch butterfly. Adult monarch butterflies feed on nectar that provides sugars and other nutrients. Monarch butterflies migrate to Mexican forests for overwintering. Overwintering monarchs reduce their metabolism and limit their feeding.

The introduction of neonicotinoids into the agricultural marketplace occurred around the same time as the introduction of GMO crops in the mid-to-late 1990s. Monsanto and Syngenta, the undisputed leaders in patented genetically engineered seeds, also have close relationships with the leading global neonic producer, Bayer. Most new commodity crops are increasingly coming to farmers with stacked traits, which means more than one transgenic alteration. These genetically engineered and transplanted traits are marketed to farmers as providing benefits such as resistance to multiple herbicides, pests, funguses, heat and drought.

Seed treatment applications are prophylactic, meaning they are used whether or not there is any evidence of pest pressures. At least 30 percent of soybean seeds planted annually (approximately 22.5 million out of 75 million acres) are pretreated with neonic insecticides (two of the primary four being imidacloprid and thiamethoxam). But corn has the highest use and acreage with around 94 percent of U.S. corn treated with a neonicotinoid. That widespread use has quickly elevated the Midwest to the highest levels of neonicotinoid use in the country. These neonicotinoids don't stay in the plants and soil however, but find their ways into the water as well. A recent U.S. Geological Survey report confirmed that neonicotinoids were common in streams throughout the Midwest.

In 1999, common milkweed, the monarch's food plant, was found in half of corn and soybean fields, but in only 8% of them a decade later. Glyphosatetolerant GM crops are grown in the same fields each year. Once absorbed, glyphosate is translocated to the roots and therefore the milkweed does not regenerate. It has been shown that clothianidin, a very long-acting systemic neonicotinoid insecticide, has contributed to the decline of monarch butterflies. USDA researchers have identified the neonicotinoid insecticide clothianidin as a likely contributor to monarch butterfly declines in North America. Neonicotinoids have been strongly implicated in pollinator declines worldwide. As shown by a report from a task force of the International Union of Nature Conservation based in Switzerland, neonicotinoids, such as clothianidin (Bayer), are a particular hazard because, unlike most pesticides, they are soluble molecules. From soil or seed treatments they can reach nectar and are found in pollen.

USDA researchers have shown that clothianidin can have effects on monarch caterpillars at doses as low as 1 part per billion. The effects seen in experiments were on caterpillar size, caterpillar weight, and caterpillar survival. The lethal dose (LC50) they found to be 15 parts per billion. The caterpillars in their experiments were exposed to clothianidin-treated food for only 36 hrs, however. The researchers therefore noted that in agricultural environments caterpillar exposure would likely be greater than in their experiments. Furthermore, that butterfly caterpillars would be exposed in nature to other pesticides, including other neonicotinoids. In sampling experiments from agricultural areas in South Dakota the researchers found that milkweeds had on average over 1 ppb clothianidin. On this basis the USDA researchers concluded that "neonicotinoids could negatively affect larval monarch populations."

Neonicotinoids are now the most widely used pesticides in the world. Neonicotinoids are neurotoxins that are partially banned in the EU. There has been negligible research on the effects of neonicotinoids on butterflies. There is a desperate need for an effective treatment to advert the destruction of monarch butterflies that has been observed over the last decade. The ramifications of the elimination of the monarch butterfly will have tremendous and as yet unforeseen negative effects on the environment. A need for a treatment is therefore long felt and unsolved. The present invention is directed to a method and system that achieves this objective.

SUMMARY OF THE INVENTION

Certain aspects of the present invention are directed to employing genes from the microbe *Ochrobactrum intermedium* such that honey bees are able to assimilate and degrade neonicotinoids. Other embodiments employ innoculaton of honey bees with a culture of neonicotinoid degrading bacteria, such as one or more of *Ochrobactrum intermedium, Agrobacterium tumefaciens* S33, *Apergillus oryzae, Pseudomonas putida* S16; *Arthrobacter nicotinovarans, microsporum gypseum, pellicularia filamentosa* JTS-208, *Pseudomonas* sp. 41; *Microsporum gypseum; Pseudomonas* ZUTSKD; *Aspergillus oryzae* 112822; and *Ochrobactrum intermedium* DN2. Preferably wherein the bacteria collection or culture comprises *Ochrobactrum intermedium*, collection number CGMCC NO. 8839. The invention further provides applications of the *ochrobactrum intermedium* to foster degradation of neonicotinoid insecticides by the honey bee while the microbe exists in the gut of the honey bee.

Honey bees host a multitude of species of microbes that positively impact bee health. The guts of honey bee workers contain a distinctive community of bacterial species. They are microaerophilic or anaerobic. These species include both Gram negative groups, such as *Gilliamella apicola* and *Snodgrassella alvi*, and Gram positive groups such as certain *Lactobacillus* and *Bifidobacterium* species. These gut bacterial species appear to have undergone long term coevolution with honey bee and, in some cases, bumble bee hosts. Prediction of gene functions from genome sequences suggests roles in nutrition, digestion, and potentially in defense against pathogens. In particular, genes for sugar utilization and carbohydrate breakdown are enriched in *G. apicola* and the *Lactobacillus* species.

CRISPR (Clustered Regularly Interspaced Short Palindromic Repeats) is a prokaryotic adaptive defense system that provides resistance against alien replicons such as viruses and plasmids. CRISPRs evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complimentary to the viral genome, mediates targeting of a Cas9 protein to a target sequence in the viral genome. The Cas9 protein cleaves and thereby silences the viral target. In preferred embodiments, rather than using CRISPR-Cas, one employs the CRISPR-associated endonuclease Cpf1. e.g. a CRISPR from *Prevotella* and *Francisella* 1 (Cpf1) nuclease for CRISPR-based genome editing (and incorporating 20150252358 to Maeder by this reference).

CRISPR has a certain protein in it called Cas9 that acts like a scissor as it recognizes specific sequences of DNA and cuts it enabling one to perform genome-editing of a bacterial genome in a person's microbiome. There exists another CRISPR system, CRISPR-Cpf1 that is even more preferred for use in microbial systems. Cpf1 is important in bacterial immunity and is well adapted to slice target DNAs. Cpf1 prefers a "TTN" PAM motif that is located 5' to its protospacer target—not 3', as per Cas9, making it distinct in having a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 merely requires a cRNA that is about 43 bases long—of which 24 nt is protospacer and 19 nt is the constitutive direct repeat sequence. In contrast, the single RNA that Cas9 needs is still about. 100 nt long. Cpf1 is apparently directly responsible for cleaving the 43-base cRNAs apart from the primary transcript.

With respect to the cleavage sites on the target DNA, the cut sites are staggered by about 5 bases, thus creating "sticky overhangs" to facilitate gene editing via NHEJ-mediated-ligation of DNA fragments with matching ends. The cut sites are in the 3' end of the protospacer, distal to the 5' end where the PAM is. The cut positions usually follow the 18th base on the protospacer strand and the 23rd base on the complementary strand (the one that pairs to the crRNA). In Cpf1 there is a "seed" region close to the PAM in which single base substitutions completely prevent cleavage activity. Unlike the Cas9 CRISPR target, the cleavage sites and the seed region do not overlap. One advantage of the present invention, as compared to techniques that rely on CRISPR systems to modify mammalian cells, is that the system and method of preferred embodiments are directed to bacterial systems—rather than eukaryotic systems. It is believed that Cpf1 may be better than Cas9 for mediating insertions of DNA, namely because its guide RNA is only 43 bases long, making it feasible to purchase directly synthesized guide RNAs for Cpf1, with or without chemical modifications to enhance stability.

CRISPR systems may be employed to insert desired genes into the above mentioned (as well as others) microbes that inhabit the honey bee gut so as to degrade particular insecticides, including neonicotinoids. The bee microbiome enhances host functions, contributing to host health and fitness. One aspect of the present invention is directed to improving honey bee fitness by modifying the honey bee microbiome, thus engineering evolved microbiomes with specific effects on the host honey bee fitness. Thus, by employing host-mediated microbiome selection, one is able to select and modify microbial communities indirectly through the host, thus influencing the honey bee microbiome and positively affecting honey bee fitness. The methods that may be used to impose artificial selection on the honey bee microbiome include various techniques known to those of skill in the art, including CRISPR-Cas and Cpf1 systems. Thus, while particular cultures of particular microbes can be purposefully included into bee populations so as to inhabit their gut microbiome, and by doing so, providing the honey bees with the ability to degrade neonicotinoids, other embodiments are directed to engineering a modification of the honey bee gut microbes that do not already possess such neonicotinoid degradation genes.

Detoxification gene inventory reduction may reflect an evolutionary history of consuming relatively chemically benign nectar and pollen. Relative to most other insect genomes, the western honey bee *Apis mellifera* has a deficit of detoxification genes. Thus, certain embodiments are directed to the development of predictable microbiome-based biocontrol strategies by providing the ability of insects such as the honey bee, to degrade or otherwise assimilate insecticides or other chemical agents, including neonicotinoids. Such a novel biocontrol strategy can not only be used to suppress pathogens but can also be effectively used to establish microbiomes in a desirable beneficial composition for particular purposes.

In certain embodiments, xenobiotic detoxification is employed to address the problems associated with the honey bee Colony Collapse Disorder. In particular embodiments, the conversion of lipid-soluble substances to water-soluble, excretable metabolites is achieved. In a primary detoxification step, a toxin structure is enzymatically altered and rendered unable to interact with lipophilic target sites. Such functionalization is effected primarily by cytochrome P450 monooxygenases (P450) and carboxylesterases (CCE), although other enzymes, including flavin-dependent monooxygenases and cyclooxygenases may also be employed. Further reactions typically involve conjugation of products of the above referenced step to achieve detoxification for solubilization and transport. Glutathione-S-transferases (GST) are the principal enzymes used, although other enzymes in insects may include glycosyltransferases, phosphotransferases, sulfotransferases, aminotransferases, and glycosidases. Nucleophilic compounds can be rendered hydrophilic by UDP-glycosyltransferases. The final stage of detoxification involves transport of conjugates out of cells for excretion. Among the proteins involved in this process are multidrug resistance proteins and other ATP-binding cassette transporters.

In the gut of the honey bee, a distinctive microbial community has been identified that is composed of a taxonomically restricted set of species specific to social bees. Despite the ecological and economical importance of honey bees and the increasing concern about population declines, the role of their gut symbionts for colony health and nutrition is largely unknown.

Long-term antibiotic treatment has caused the bee gut microbiota to accumulate resistance genes, drawn from a widespread pool of highly mobile loci characterized from pathogens and agricultural sites. 50 years of using antibiotics in beekeeping in the United States has resulted in extensive tetracycline resistance in the gut microbiota. Since the 1950s, the antibiotic oxytetracycline has been widely applied to colonies of bees in the United States to control larval foulbrood diseases caused by the bacteria *Melissococcus pluton* and *Paenibacillus larvae*; oxytetracycline was the only antibiotic approved for use in beekeeping until 2005.

When antibiotics are used for controlling infections by pathogens, they also impact other microbes, including the beneficial bacteria present in healthy hosts. The selective force imposed by an antibiotic can cause the accumulation of resistance determinants, which are often encoded on mobile genetic elements that are readily transferred among community members. The impact of antibiotics on the gut microbiota of honey bees is a particular concern, since gut communities may act as reservoirs for resistance genes that can be transferred to pathogens and also since perturbation of gut microbiota by antibiotic treatments could disrupt functions beneficial to the honey bee, butterflies and bats. Thus, in certain aspects of the present invention, restoring antibiotic resistance is one objective and this can be achieved via CRISPR-Cas modifications.

Compared to the gut microbiota of humans and other mammals, the honeybee gut microbiota provides a distinctive and relatively simple bacterial community. The honeybee has eight characteristic bacterial species that together comprise over 95% of the gut bacteria in adult worker bees. The eight bacterial species known to dominate the honeybee gut microbiota, primarily the Gram-negative members of this community are referred to via previous designations: "Alpha1" and "Alpha2" from the *Alphaproteobacteria*, *Snodgrassella alvi* from the Betaproteobacteria, *Gilliamella apicola* and "Gamma2" from the Gammaproteobacteria, "Firm4" and "Firm5" from the Firmicutes, and "Bifido" from the Bifidobacteriaceae. Any one or more of these bacteria can be modified to express particular genes that have been shown (for example by its inclusion in the bacteria *Ochrobactrum intermedium*, to degrade neonicotinoids in a manner that preserves honey bee health.

The following references are incorporated by reference in their entireties to provide requisite written description and enablement for various embodiments of the various embodiments of the present invention. Certain embodiments of the present invention involve the use of CRISPR-Cas or Cpf1 or other related systems to modify the microbiomes of the insects and animals as described herein, including specifically honeybees, such that the insects/animals can assimilate (e.g. by degradation) particular pesticides that would otherwise cause them harm or damage.

Neonicotinoids are a class of insecticides, which includes imidacloprid, acetamiprid, thiacloprid, dinotefuran, nitenpyram, thiamethoxam, and clothianidin, and have a high target specificity to insects (Ensley, 2012c). The neonicotinoids act on postsynaptic nicotinic acetylcholine receptors (nAChRs). In insects, these receptors are located entirely in the CNS.

It is well recognized that nicotine is a highly toxic alkaloid primarily found in the plant family Solanaceae, including tomato, potato, green pepper and tobacco. It is a broadly effective defense against herbivores, with a mode of action resembling that of synthetic neonicotinoids; and has been used as a non-synthetic insecticide in the form of tobacco tea in organic farming methods (Isman et al., 2006). Nicotine mimics acetylcholine at the neuromuscular junction in mammals, causing twitching, convulsions and even death (Steppuhn et al., 2004; Tom izawa et al., 2003). In susceptible insects, the same mode of action is observed in the ganglia of the central nervous system. One of skill in the art, with the guidance provided herein, including the references incorporated herein by reference, can apply various transgenic technologies of molecular biology, genetics and other disciplines—including CRISPR-Cas and Cpf1 systems, to modify microbes, especially gut microbes resident in particular insect or animals, to provide the ability to degrade nicotinoids before they adversely affect the insects/animals.

The gene editing technology known as Clustered Regularly Interspaced Short Palindromic Repeats (CRISPR) and the CRISPR-associated protein 9 (Cas9), referred to as: (CRISPR/Cas9), has demonstrated exponential acceptance in the scientific community and is applied across a wide variety of genetic applications. While RNAi technology can suppress transcripts of gene expression, the CRISPR/Cas9 system can perform precision insertions and deletions in the eukaryotic genome that are inheritable. As described herein, these two technologies (RNAi and CRISPR/Cas9) provide unique advantages for addressing how to ameliorate pathogens.

CRISPR/Cas9 gene editing is a powerful tool to modify bacterial genomes and can be applied to genetically alter host-associated bacteria. Use of a CRISPR system may be employed to delete outer membrane proteins, as well as employed to achieve the deletion of other proteins to impair the ability to form biofilms. Moreover, integration of genes into the bacterial genome can be exploited to develop control strategies. CRISPR/Cas9 and Cpf1 system technology can be employed for genetic manipulation of gut microbes.

As one of skill in the art appreciates, the CRISPR/Cpf1 system employs the smaller Cpf1 enzyme. Cpf1 is a smaller and simpler endonuclease than Cas9, overcoming some of the CRISPR/Cas9 system limitations. These advantages allow it to more efficiently edit the genomes of different organisms, See, e.g. Zetsche et. al, 2015). The *G. apicola* microbe of the honeybee gut, for example, includes CRISPR elements, making it suitable and available for modification employing the CRISPR systems described herein, especially in view of the knowledge of one of skill in the art with respect to the genomics of the honeybee gut microbes, see e.g. Kwong, et. al, PNAS (2014), describing the abundance in *G. apicola* genomes of CRISPR elements.

CRISPR (Clustered Regularly Interspaced Short Palindromic Repeats) is a prokaryotic adaptive defense system that provides resistance against alien replicons such as viruses and plasmids. CRISPRs evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complimentary to the viral genome, mediates targeting of a Cas9 protein to a target sequence in the viral genome. The Cas9 protein cleaves and thereby silences the viral target. In preferred embodiments, rather than using CRISPR-Cas, one employs the CRISPR-associated endonuclease Cpf1. e.g. a CRISPR from *Prevotella* and *Francisella* 1 (Cpf1) nuclease for CRISPR-based genome editing. *Prevotella* sp. C561 SEQ ID NO: 184 250 67 357 425 78 357 425 78 gi|345885718|ref|ZP_08837074.1; *Prevotella timonensis* CRIS 5C-B1 SEQ ID NO: 170 208 39 328 375 61 328 375 61 gi|282880052|ref|ZP_06288774.1 (and incorporating 20150252358 to Maeder by this reference). Spacers in a CRISPR cassette confer immunity against viruses and plasm ids containing regions complementary to the spacers and hence, they retain a footprint of interactions between prokaryotes and their viruses in individual strains and ecosystems. To comply with written description and enablement requirements, incorporated herein by the following references are the following patent publications: 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849 and WO 2013026000 to BRYAN; 20200318139 to Gersbach, et. al.; 20160024510 to Bikard, et. al.; 20190015528 to Moran, et. al.

There is a diversity of CR/SPR-Cas systems based on the set of cas genes and their phylogenetic relationship. The most recent classification system (Makarova et al. Nat Rev Microbiol. 2015 Sep. 28. doi: 10.1038/nrmicro3569) defines five different types (I through V) with many possessing multiple subtypes. The Type I systems represent the most common type of CR/SPR-Cas systems, representing over 50% of all identified systems in both bacteria and archaea. Type I systems are further divided into six subtypes: I-A, I-B, I-C, I-D, I-E, and I-F. While the exact set of proteins between these systems varies, they share a common framework: all of the systems encode an endoribonuclease called Cas3, which is split into two proteins (Cas3, Cas3") for I-A and I-B systems. Most of the other proteins form a multi-subunit complex called Cascade (for complex associated with antiviral defense) that is responsible for processing the CRISPR RNAs and binding target DNA. The only requirements for DNA binding are that (1) the target substantially match the spacer portion of the CRISPR RNA and (2) the target is flanked on its 5' end by a protospacer-adjacent motif (PAM). The PAM is recognized by one of the Cas proteins within Cascade (e.g., the Cse1 protein in the Type I-E Cascade), which then unwinds the flanking DNA to evaluate the extent of base pairing between the target and the spacer portion of the CRISPR RNA. Sufficient recognition leads Cascade to recruit and activate Cas3. Cas3 then nicks the non-target strand and begins degrading the strand in a 3'-to-5' direction (Gong et al. Proc Natl Acad Sci USA. 111(46):16359-64 (2014).

In various aspects of the present invention, CRISPR is employed to modify aspects for both bacterial and helminthes gene expression such that undesired normally transcribed proteins are excised or precluded from being expressed, thus precluding the deleterious effects of such proteins. Thus, normally dangerous species of bacteria and helminthes (from a perspective of such bacteria or helminths causing disease) can be modified so that such undesired effects of bacterial and helminths infection are disrupted or deleted or lessened in a fashion that still permits the beneficial aspects of bacterial and helminths proteins to be maintained.

Various embodiments of the present invention combine each of the above referenced four FLVR bacteria and using CRIPR, pathogenic and/or toxic elements are excised to preclude detrimental health issues that would normally be encountered using one or more of such bacteria.

In certain embodiments of the present invention, antibiotic resistance of certain bacteria is modulated by employment of CRISPR to insert into the genome of a bacteria antibacterial sensitivity such that it can selectively be killed, if necessary.

In particular embodiments, directed to a topical composition of a bacterial and/or helminthes containing composition, such composition includes cells that have been transformed by use of CRISPR to delete particular undesired attributes of wild-type species, including the expression of disease causing proteins.

The use of CRISPR to tailor bacterial and helminths components to either add desired characteristics and/or to delete known deleterious aspects of such bacteria or helminths, provides a novel system and method for treating a variety of diseases such that bacteria and helminths that would normally be considered too dangerous to employ as an agent is now rendered available for such purposes.

In various embodiments, DNA is injected into bacteria to restore antibiotic sensitivity to drug-resistant bacteria, and to also prevent the transfer of genes that create that resistance among bacteria. The CRISPR-CAS system may also be employed to render certain bacteria sensitized to certain antibiotics such that specific chemical agents can selectively choose those bacteria more susceptible to antibiotics, see, e.g. U.S. Pat. Publication No. 2013/0315869 to Qimron, which is incorporated in its entirety by this reference.

The microbiome of an individual is disrupted by antibiotics and thus, the employment of CRISPR as a way to bypass common modes of multidrug resistance, while being selective for individual strains, is employed in various embodiments of the present invention to attain the benefits derived by the presence of particular bacteria and helminths, including the triggering of desired immune development by newborns and other individuals, (e.g. those with multiple sclerosis, etc.). CRISPR-Cas systems employ CRISPR RNAs to recognize and destroy complementary nucleic acids. In various embodiments of the present invention, CRISPR-Cas systems are used as programmable antimicrobials to selectively kill bacterial species and strains such that desired selected targets can be focused on such that virtually any genomic location may be a distinct target for CRISPR-based antimicrobials, and that, in conjunction with an appropriate delivery vehicle, such as those employed by Bikard et al. and Citorik et al., one is able to effectively deploy a CRISPR-Cas system as an antimicrobial agent.

Another aspect of certain embodiments include making synthetic CRISPR-containing RNAs that target genes of interest and using them with Cas enzymes. The specificity of CRISPR-Cas systems permits one to design methods to target a single bacterial species so that only essential genes form that one species is targeted and cut up. CRISPR-Cas systems are employed in various ways in the many embodiments of the present invention to retain the beneficial bacterial communities intact and to offer protection against undesired bacterial pathogens.

CRISPR has a certain protein in it called Cas9 that acts like a scissor as it recognizes specific sequences of DNA and cuts it enabling one to perform genome-editing of a bacterial genome in a person's microbiome. There exists another CRISPR system, CRISPR-Cpf1 that is even more preferred for use in microbial systems. Cpf1 is important in bacterial immunity and is well adapted to slice target DNAs. Cpf1 prefers a "TTN" PAM motif that is located 5' to its protospacer target—not 3', as per Cas9, making it distinct in having a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 merely requires a cRNA that is about 43 bases long—of which 24 nt is protospacer and 19 nt is the constitutive direct repeat sequence. In contrast, the single RNA that Cas9 needs is still about. 100 nt long. Cpf1 is apparently directly responsible for cleaving the 43-base cRNAs apart from the primary transcript.

With respect to the cleavage sites on the target DNA, the cut sites are staggered by about 5 bases, thus creating "sticky overhangs" to facilitate gene editing via NHEJ-mediated-ligation of DNA fragments with matching ends. The cut sites are in the 3' end of the protospacer, distal to the 5' end where the PAM is. The cut positions usually follow the 18th base on the protospacer strand and the 23rd base on the complementary strand (the one that pairs to the crRNA). In Cpf1 there is a "seed" region close to the PAM in which single base substitutions completely prevent cleavage activity. Unlike the Cas9 CRISPR target, the cleavage sites and the seed region do not overlap. One advantage of the present invention, as compared to techniques that rely on CRISPR systems to modify mammalian cells, is that the system and method of preferred embodiments are directed to bacterial systems—rather than eukaryotic systems. It is believed that Cpf1 may be better than Cas9 for mediating insertions of DNA, namely because its guide RNA is only 43 bases long, making it feasible to purchase directly synthesized guide RNAs for Cpf1, with or without chemical modifications to enhance stability.

The CRISPR system may be employed in various embodiments to strengthen antibiotics or to kill the bacteria altogether. By removing the bacteria's genes that make them antibiotic-resistant, CRISPR can boost the effectiveness of existing drugs. CRISPR can also be used to remove a bacteria's genes that make them deadly and facilitate RNA-guided site-specific DNA cleavage. Analogous to the search function in modem word processors, Cas9 can be guided to specific locations within complex genomes by a short RNA search string.

In certain embodiments, various particular bacterial species are focused on to delete or modulate their gene expressions, such species including the following: *Streptococcus; Escherichia coli, Streptococcus pyogenes*, and *Staphylococcus epidermidis*. This prokaryotic viral defense system has become one of the most powerful and versatile platforms for engineering biology.

In various embodiments, the CRISPR-Cas systems is employed to control the composition of the gut flora, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas systems. Because of the sequence specificity of targeting, CRISPR-Cas systems may be used to distinguish strains separated by only a few base pairs. Thus, in many embodiments, CRISPR-Cas systems provide for the selective removal of microorganisms to trigger certain predictable development of the immune system.

The specificity of targeting with CRISPR RNAs may be employed to readily distinguish between highly similar strains in pure or mixed cultures. Thus, in certain embodiments, varying the collection of delivered CRISPR RNAs is employed to quantitatively control the relative number of individual strains within a mixed culture in a manner to circumvent multidrug resistance and to differentiate between pathogenic and beneficial microorganisms.

In certain other aspects, particular embodiments of the present invention are directed to the use of CRISPR to excise certain prior infectious adenovirus DNA sequences that are considered responsible for the increased obesity of individuals harboring the same. Reference is made to Kovarik, U.S. Pat. No. 8,585,588, "Method and system for preventing virus-related obesity and obesity related diseases." After determining whether one has been infected with an obesity causing virus, the viral DNA can then be excised via CRISPR to remove the previously inserted DNA, thus effectively reducing if not eliminating the adenovirus gene from the individual. Thereafter, to avoid being infected with such adenovirus again, practice of the method as set forth in U.S. Pat. No. 8,585,588 will lessen, if not prevent, reacquisition of such obesity causing DNA.

Controlling the composition of microbial populations is important in the context of desiring to expose expectant mothers to particular species of bacterial and other microbes, helminthes, etc. and especially those that have not been previously exposed to antibiotics, antimicrobial peptides, and lytic bacteriophages. Use of CRISPR-Cas provides a generalized and programmable strategy that can distinguish between closely related microorganisms and allows for fine control over the composition of a microbial population for use in the present invention. Thus, the RNAdirected immune systems in bacteria and archaea called CRISPR-Cas systems is employed in various embodiments of the present invention to selectively and quantitatively remove individual bacterial strains based on sequence information to enable the fine tuning of exposure of desired antigens present in an Amish soil microbial consortia. Thus, such genome targeting using CRISPR-Cas systems allows one to specifically remove individual microbial species and strains, leaving other microbes to trigger an infant's immune system in desired ways.

In various embodiments, it is desirable to remove—using CRISPR-Cas systems—particular pathogenic bacteria and/or simply the pathogenic portions of such bacteria—while sparing other desired commensal bacteria, in order to provide exposure to desired immune developing proteins.

In various embodiments, one of skill in the art will appreciate that removal of particular strains of bacteria may be achieved using both type I and type II CRISPR-Cas systems, given the distinction between these systems being that type I systems cleave and degrade DNA through the action of a 3'-to-5' exonuclease, whereas type II systems only cleave DNA. In still other embodiments, multiple guide RNAs can also be used to target several genes at once. The use of effector fusions may also expand the variety of genome engineering modalities achievable using Cas9. For example, a variety of proteins or RNAs may be tethered to Cas9 or sgRNA to alter transcription states of specific genomic loci, monitor chromatin states, or even rearrange the three-dimensional organization of the genome.

On aspect of many embodiments of the present invention include the use of specialized viruses to supply CRISPR/Cas to rid bacteria of antibiotic-resistance plasmids and/or other virulence factors. Virulence factors of Gram-negative anaerobes such as *Prevotella* include, for example, fimbria, hemolysins, adhesions and hemagglutinins. These bacteria commonly produce immunoglobulin-degrading enzymes and some produce tissue-degrading enzymes. Additionally, bacteria of the genus *Prevotella* are often resistant to antibiotics, such as tetracycline, erythromycin, and .beta.-lactam antibiotics. In practice, a *Prevotella*-targeting lambda phage is created that encodes the CRISPR genes plus spacers that target two conserved .beta. lactamases, enzymes that confer resistance to .beta.-lactam antibiotics. Once integrated into the *Prevotella* genome, the phage prevents the transfer of .beta. lactamase-encoding plasm ids and can also delete these plasm ids from individual bacterial cells. These lambda phage-encoding bacteria then become sensitive to treatment with antibiotics.

CRISPR-Cas can be used on the various identified microbiome constituents to modify gene expression, including cutting of a gene, repress or activate a gene, etc. It can be employed to deliver desired regulators or any protein to a desired place on a genome of a microbe, thus permitting one to tailor the attributes of the microbiome to promote the health thereof. Because CRISPR-Cas acts before transcription occurs, it is able to be employed to target regulatory and other elements on the DNA of microbes that make up the microbiome. In certain embodiments, CRISPR-Cas is employed to deliver fluorescent markers to certain DNA sequences, thus permitting one to determine whether any particular sample has been treated in accordance with the present invention, thus ensuring, for example, identity of various materials, safety issues, etc.

In particular embodiments, the use of CRISPR systems to target virulence factors of bacteria is employed to enable the maintenance and destruction of such populations when desired. For example, some of the virulence factors that may be targeted include the following: Gingipain; Capsular polysaccharide; fimbriae; etc. In various embodiments, *Prevotella intermedia* ATCC 25611 and/or *Prevotella*-345885718 *Prevotella* sp. C561 are employed in the present invention, especially in embodiments that employ CRISPR systems to reduce the virulence factors thereof. While antibiotic therapy is non-discriminatory in its action, the use of CRISPR systems permits one to fine tune the selective elimination of particular microbes. One survival mechanism of *Prevotella* cells is the possession of natural antibiotic resistant genes, which prevent extermination. Modification of *Prevotella* using a CRISPR-system, provides a way to render *Prevotella* susceptible to antibiotics, thus permitting its regulation. Having said this, certain antibiotics found useful in treating *Prevotella* include metronidazole, amoxycillin/clavulanate, ureidopenicilins, carbapenems, cephalosporins, clindamycin, and chloramphenicol.

In various embodiments of the present invention, bacterial DNA is altered from pathogenic to non-pathogenic using various methods known to those of skill in the art. One such method is the employment of a CRISPR-Cas to introduce a mutation to the bacterial genome, and/or to specific genes encoding for membrane or secretory products, and/or other genes that regulate virulence genes. Interference with the expression or efficacy of various pathogenic characteristics of certain bacteria, such as by affecting particular virulence factors possessed by bacteria, viruses, fungi, and protozoa, including but not limited to immunoglobulin (Ig) proteases, capsules, endotoxins, mobile genetic elements, plasmids, and bacteriophages. Specifically, and to provide representative examples, virulence factors for *Staphylococcus aureus* include hyaluronidase, protease, coagulase, lipases, deoxyribonucleases and enterotoxins. Examples for *Streptococcus pyogenes* are M protein, lipoteichoic acid, hyaluronic acid capsule, destructive enzymes (including streptokinase, streptodornase, and hyaluronidase), and exotoxins, including streptolysin. Examples for *Listeria monocytogenes* include internalin A, internalin B, lysteriolysin O, and actA. Examples for *Yersinia pestis* include an altered form of lipopolysaccharide, and YopE and YopJ pathogenicity. Other virulence factors include factors required for biofilm formation (e.g. sortases) and integrins (e.g. beta-1 ad3). In addition to bacteria, helminthes possess similar factors, such as neutrophil inhibitory factor. Thus, one aspect of the present invention is to employ CRISPR systems to achieve interference with specific virulence factors or with regulatory mechanisms that control the expression of multiple virulence factors, and in such a manner, provide a way for such microbes to positively affect a person's immune system without attendant pathogenicity. In certain embodiments this may take the form of employing CRISPR loci to control, for example, the dissemination of antibiotic resistance in bacterial species, such as staphylococci. For example, CRISPR targeting of *Streptococcus pneumoniae* capsule genes, essential for pneumococcal infection, provides a way to thwart bacteria virulence and pathogenic effects. In certain embodiments, the CRISPR-Cas system is effectively employed as a regulator of gene expression and in such manner, provides a way for bacteria, especially pathogenic bacteria, instead of being eliminated by the use of broad based antibiotics, are transformed into non-pathogenic microorganisms, thus maintaining the positive attributes that they provide in a microbiome of an individual.

In accordance with various embodiments of the present invention, multiple species of Proteobacteria that are native to the gut microbiomes of honey bees (*Apis mellifera*) and bumble bees (*Bombus* sp.) can be modified to achieve desired expression of proteins. Expressing fluorescent proteins in *Snodgrassella alvi, Gilliamella apicola, Bartonella apis*, and *Serratia* strains enables one to visualize how these bacteria colonize the bee gut and permits one to demonstrate CRISPRi repression in *B. apis* and to use Cas9-facilitated knockout of an *S. alvi* adhesion gene to show that it is important for colonization of the gut. The gut microbiome influences the health of bees and one of skill in the art, employing available bee microbiome toolkits, can effectively engineer bacteria found in other natural microbial communities. U.S. Pat. Publication Nos. 20180177160 to Wagoner, et. al.; 20180208977 to Doudna, et. al.; and 20180163265 to Zhang, et. al, are incorporated herein by this reference.

One of skill in the art will appreciate the employment of Nicotine-Degrading Gene Clusters and the use of CRISPR systems to insert the same into different species of microbes typically resident in the gut of bees, bats and/or butterflies. The references below are all incorporated herein by this reference to provide written description and enablement for the various embodiments of the present invention. For example, others have generated the complete genome sequence of the nicotine-degrading bacterium *Shinella* sp. Previous studies showed that a novel 6-hydroxy-nicotine oxidase, NctB, was responsible for the degradation of 6-hydroxy-nicotine to 6-hydroxypseudooxynicotine (Qiu et al., 2014). The nctB gene (locus tag shn_30305) was found on the plasmid pShin-05. The nctB gene, as well as genes homologous to vppA (nicotine hydroxylase gene), vppE (2,5-dihydroxypyridine dioxygenase gene) from *Ochrobactrum* sp. strain SJY1 (Yu et al., 2015) and pno (6-hydroxypseudooxynicotine oxidase gene) from *Agrobacterium tumefaciens* S33 (Li et al., 2016), appeared in an 50 kb region of DNA with a GC content of 56.6%. Similarly, Wang et al. (2013) described the acetamiprid degradation kinetics using the *Ochrobactrum* sp. bacterial strain, which is capable of degrading acetamiprid from 0 to 3000 mg L-1 within 48 h. See also, Royal Society of Chemistry (RSC Adv., 2017, 7, 25387). Bacterial species belonging to *Ochrobactrum* genus are opportunistic pathogens due to insertion and deletion of genes. The *Ochrobactrum intermedium* genome sequence was documented in 2009. Still other researchers, e.g. Shi-Lei Sun, et al., have written about the biodegradation of the neonicotinoid insecticide acetamiprid by the bacterium Variovorax boronicumulans CGMCC 4969 and its enzymatic mechanism. The metabolism of thiamethoxam, a neonicotinoid pesticide, has been described by Coulon, et. al, (2017) such that one of skill in the art would appreciate that such a nitro-substituted neonicotinoid can be degraded. The metabolism of the widely used neonicotinoid insecticide acetamiprid (ACE) can be degraded via the employment of the SCL3-10 nitrile hydratase beta subunit gene, see, e.g. Imidacloprid is degraded by CYP353D1v2, a cytochrome P450. wiley.com/doi/10.1002/ps.4570/full (2017). Parte, et al., reviews the microbial degradation of pesticides in the African Journal of Microbiology Research (2017). Madhuban et al. (2011) describes the degradation of imidacloprid and metribuzin; Singh DK (2008) describes the biodegradation and bioremediation of pesticides in the Indian J. Microbiol.48:35-40; Madhuban G, et. al. (2011) describe the biodegradation of imidacloprid and metribuzin by *Burkholderia cepacia* strain CH9 in Pestic. Res. J. 23(1):36-40; Hegde, et. al. "CRISPR/Cas9-mediated gene deletion of the ompA gene in an *Enterobacter* gut symbiont impairs biofilm formation and reduces gut colonization of *Aedes aegypti* mosquitoes," bioRxiv, (2018); Sinisterra-Hunter, et. al, "Towards a Holistic Integrated Pest Management Lessons Learned from Plant-Insect Mechanisms in the Field"; Ruan et al. "Isolation and characterization of a novel nicotinophilic bacterium, *Arthrobacter* sp. aRF-1 and its metabolic pathway," *Biotechnology and Applied Biochemistry* (2018); U.S. Patent publicatoin No. 20180119132 to Hutchison, III et. al., Leonard, et. al., Genetic Engineering of Bee Gut Microbiome Bacteria with a Toolkit for Modular Assembly of Broad-Host-Range Plasmids, *ACS Synth. Biol.*, (2018).

The mechanism of degradation and regulation of nicotinoid degrading enzyme genes has been clarified at the DNA level, and degradation genes have been cloned and microorganisms prepared, resulting in identification and study of degradation plasmids and pesticide pollution-degrading enzymes, such that such the gene pool, coupled with the use of modern genetic engineering, permits one of skill in the art to build more efficient degradation engineered bacteria. US patent publication No. 20170035820 to Stamets et al., employing integrative fungal solutions for protecting bees and overcoming colony collapse disorder (CCD); Probeeotics UBC Igem (2015); Critical Reviews in Biotechnology, where pesticide degraders were unraveled via stable isotope probing; U.S. patent publication No. 20180216123 to Anand, et. al., who explore OCHROBACTRUM-MEDIATED TRANSFORMATIONs of cells, including the nuclease-mediated genome modification with *Ochrobactrum* to make genome modifications mediated by CRISPR-Cas nucleases, further described in WO 2013/141680, US 2014/0068797, and WO 2015/026883, each of which is incorporated herein by reference in their entireties, including techniques for the transformation of *Ochrobactrum* by employing CRISPR-Cas9 Nuclease and Endonuclease-Mediated Genome Modifications Using Transfer Cassettes and/or Helper Plasm ids, thus improving CRISPR-Cas9 genome editing. Transfer cassettes including, but not limited to RepABC, pRi, pVS1, RK2 can be used to modulate the amount of DNA molecules delivered to cells used in CRISPR-Cas9 genome editing. PCT/US2016/049135 is also incorporated herein by reference with respect to nicotinoid degrading genes. Numerous genes (both host and symbiont) and the proteins they encode identified herein as being associated with nicotinoid-pathogen synergy, such as those described in U.S. patent publication no. 20180020678, incorporated herein by this reference, are subject to being regulated by the use of CRISPR-systems, such that the nicotinoid degradation can proceed to render the hosts (honey bees, bats, butterflies, etc.) less susceptible to nicotinoids. See also, The Biological Degradation of Nicotine by Nicotinophilic Microorganisms Beiträge zur Tabakforschung International-Contributions to Tobacco Research.html (January 2015); Sarfraz Hussain, et. al., "Bacterial biodegradation of neonicotinoid pesticides in soil and water systems," *FEMS Microbiology Letters*, Volume 363, Issue 23, (2016).

The important enzymes involved in degrading neonicotinoid insecticides include those in the P450 superfamily, with one of skill in the art able to select which of the P450 clades is the right candidate for genetic engineering of particular microbes to affect the degradation of a particular pesticide in a particular insect or animal. Several pesticide degrading genes are known, including pyrethroid-hydrolyzing genes from *Klebsiella* sp. ZD112, *Sphingobium* sp. JZ-1 and metagenome. The pyrethroid-degrading strain *Ochrobactrum anthropi* YZ-1 and the expression of the gene pytZ which encodes a pyrethroid-hydrolyzing carboxylesterase can be employed as the purified enzyme has been studied for its substrate specificity, stability, optimal temperature and pH.

Incorporated by reference in their entireties are the following: Zhai, et. al. Molecular cloning, purification and biochemical characterization of a novel pyrethroid-hydrolyzing carboxylesterase gene from *Ochrobactrum anthropi* YZ-1, Journal of Hazardous Materials, June 2012, Pages 206-212; P. C. Wu, et. al., Molecular cloning, purification, and biochemical characterization of a novel pyrethroid-hydrolyzing esterase from *Klebsiella* sp. strain ZD112, J. Agric. Food Chem., 54 (2006), pp. 836-842; B. Z. Wang, et. al., Cloning of a novel pyrethroid-hydrolyzing carboxylesterase gene from *Sphingobium* sp. JZ-1 and characterization of the gene product, Appl. Environ. Microbiol., 75 (2009), pp. 5496-5500; G. Li, et al., Molecular cloning and characterization of a novel pyrethroid-hydrolyzing esterase originating from the metagenome, Microb. Cell Factories, 7 (2008); S Chen et al. Pathway and kinetics of cyhalothrin biodegradation by *Bacillus thuringiensis* strain ZS-19, Scientific reports, 2015—nature.com; A S Pankaj, et. al., Novel pathway of cypermethrin biodegradation in a *Bacillus* sp. strain SG2 isolated from cypermethrin-contaminated agri-culture field; 3 Biotech, 2016—ncbi.nlm.nih.gov; H Itoh, et. al., Detoxifying symbiosis: microbe-mediated detoxification of phytotoxins and pesticides in insects, Natural product reports, 2018—pubs.rsc.org; T Gong, et. al., An engineered *Pseudomonas putida* can simultaneously degrade organo-phosphates, pyrethroids and carbamates, Science of The Total . . . , 2018—Elsevier.

Another aspect of the present invention is directed to addressing how we can stem the tide of bat decline by modifying the gut microbiota of bats so as to enable the bats to degrade various materials, including neonicotinoids, thus providing a method and system to assist in the survival and reproduction of bats. Both skin and gut microbiomes are involved in certain embodiments of the present invention. In certain embodiments, a treatment to prevent or at least reduce the occurrence and ramifications from White-nose syndrome, caused by the fungal skin pathogen *Pseudogymnoascus destructans*, is set forth, such treatment holding promise to avert the threat that several hibernating bat species may go extinct and offering one of the only effective treatment strategies for such condition. The skin microbiome of the bat is believed to play an important role in an effective treatment for WNS. In certain embodiments, bacteria of the genus *Pseudomonas* are employed to adversely affect the growth of the *P. destructans*. While in certain embodiments, bacteria found naturally occurring on bats are employed to inhibit the growth of *P. destructans*, in other embodiments, modified bacteria, preferably via the use of a CRISPR-Cas or Cpf1 system, is employed to enhance the growth of particular bacteria on the skin of bats, so as to counter the effects of WNS, notably by inhibiting the growth of *P. destructans*. These modified bacteria are thus employed as a skin probiotic to protect bats from white-nose syndrome.

Yet another aspect of the present invention is directed to addressing how to stem the tide of butterfly decline, and in particular Monarch butterfly declines, by modifying the gut microbiota of monarch butterflies so as to enable the butterflies to degrade neonicotinoids, thus providing a method and system to assist in the survival and reproduction of the monarch butterfly. Herein after, while emphasis is placed on Monarch butterflies, one of skill in the art will appreciate the application of the present invention to other pollinators, such as other butterflies, moths, etc. Monarch butterflies frequently consume milkweed in and near agroecosystems and consequently may be exposed to pesticides like neonicotinoids. One aspect of the present invention is directed to addressing how to stem the tide of monarch butterfly decline by modifying the gut microbiota of monarch butterflies so as to enable the butterflies to degrade neonicotinoids, thus providing a method and system to assist in the survival and reproduction of the monarch butterfly.

Numerous genes (both host and symbiont) and the proteins or contigs they encode are identified herein as being associated with nicotinoid-pathogen synergy, as further described in U.S. patent publication no. 20180020678, incorporated herein by this reference. By regulating the expression of one or more of these identified genes, proteins, and/or contigs, e.g. via the use of CRISPR-systems, the nicotinoid degradation can proceed to render the hosts (honey bees, bats, butterflies, etc.) less susceptible to nicotinoids.

Fipronil [5-Amino-3-cyano-1-(2,6-dichloro 4 trifluoromethylphenyl)-4-trifluoromethyl sulfinyl pyrazole is a phenyl pyrazole insecticide first synthesized by Rhoˆne Poulenc Ag Company (now Bayer Crop Science) in 1987, introduced for use in 1993 and registered in the U.S. in 1996. Fipronil is labeled for use in large number of crops and is effective against a wide range of insect pests. It has been evaluated against over 250 insect pests and on more than 60 crops worldwide. Fipronil, as marketed under the name Regent, has been used against lepidopteran and orthopteran pests on a wide range of field and horticultural crops and coleopteran larvae in soils. Fipronil acts on gamma amino butyric acid (GABA) receptor, the principal nerve transmitter in insects, preventing the inhibition of GABA. Biological studies have shown that fipronil interferes with the passage of chloride ions through the gamma amino butyric acid disrupting central nervous system (CNS) activity. Fipronil is very highly toxic for crustaceans, insect and zooplankton, as well as bees, termites, rabbits, the African tilapia, the fringe-toed lizard and certain groups of gallinaceous birds.

Microorganisms can be helpful when it comes to the elimination of pesticides. The increasing number of pesticides used in agriculture has recently acquired great importance due to the contamination of the environment. Microorganisms are of great importance in environmental cleaning and insecticide degradation. The bacterial *Paracoccus* sp. has been identified for the degradation of fipronil. *Paracoccus* sp. have been described as bacteria capable of utilizing carbon and nitrogen as source of energy from the fipronil. Cultures of Orchrobacterium sp., *Arthrobacter* sp. and *Burkholderia* sp. isolated and identified on the basis of 16s rDNA gene sequences, have shown in situ biodegradation of aendosulfan, a-endosulfan and b-endosulfan, respectively. In certain embodiments of the present invention, modifications can be brought about in certain microbes to encourage the organisms to degrade various pesticides at a faster rate. Such degradation by certain microbes can be achieved by introducing such microbes into the gut microbiome of particular insects such that such organisms can provide the benefits of degradation of particular insecticides in a manner that precludes the harm to the insect's health that would otherwise occur. In certain embodiments, *Paracoccus* sp. is employed to degrade fipronil. While introduction into the gut microbiomes of particular insects of particular bacteria and microbes known to degrade particular insecticides is one aspect of several embodiments of the present invention, other embodiments entail the incorporation of specific genes from organisms known to degrade particular pesticides such that those same pesticide degradation abilities are incorporated into the resident and native bacterial flora of particular insect gut microbiomes. This can be achieved without undue experimentation by one of ordinary skill in the art as the employment of CRISPR systems, in conjunction with knowledge of particular genomes of bacteria known to degrade certain pesticides, provides the requisite knowledge and guidance to effect particular genomic transformation and manipulation of host gut microbiomes such that degradation of pesticides by such bacteria is made possible. Specifically, there are acknowledged bacteria that possess the ability to degrade fipronil and the genomes of such bacteria are known. For example, the genome sequence of *Paracoccus denitrificans* strain ISTOD1 of 4.9 Mb has been elucidated and thus, one of skill in the art can readily employ CRISPR systems to manipulate and to incorporate the genes from such microbe involved in the degradation of fipronil so that the microbes resident in the gut microbiome of insects, and in particular of honey bees (but as described herein, also of monarch butterflies and bats, etc.), would then possess the ability to degrade pesticides, specifically fipronil, that are causing them such current harm. See e.g., Medhi, et. al, Genome Sequence of a Heterotrophic Nitrifier and Aerobic Denitrifier, *Paracoccus denitrificans* Strain ISTOD1, Isolated from Wastewater, Genome Announc. 2018 April; 6(15): e00210-18. See also, Kumar, et. al., Biodegradation of Fipronil by *Paracoccus* sp in Different Types of Soil, Bulletin of Environmental Contamination and Toxicology 88(5):781-7 (2012), both of which are incorporated herein by this reference.

In a similar manner as described herein, still other genomes of microbes may be employed to achieve the biodegradation of fipronil by gut microbes in particular insects, including the honeybee, for example: Degradation of fipronil by Stenotrophomonasacidaminiphila, Uniyal, et. al, *Degradation of fipronil by Stenotrophomonasacidaminiphila isolated from rhizospheric soil of Zea mays,* 3 *Biotech.* 2016 June; 6(1): 48; Mandal K, et. al, *Microbial degradation of fipronil by Bacillus thuringiensis, Ecotoxicol Environ Saf.* 2013 July; 93:87-92, also incorporated herein by this reference. Huang, et. al., Genome Sequencing and Comparative Analysis of *Stenotrophomonas acidaminiphila* Reveal Evolutionary Insights Into Sulfamethoxazole Resistance, Front Microbiol. 2018; 9: 1013.

The last few years have witnessed an unprecedented increase in the number of novel bacterial species that hold potential to be used for metabolic engineering. Historically, only a relatively few bacteria have attained the acceptance and widespread use in industrial bioproduction of compounds. Now, however, with the ability to perform targeted genome engineering of bacterial chassis, such as via CRISPR systems, synthetic biology is able to provide bacteria that can accomplish degradation of compounds in an unprecedented fashion.

Decades of research considerably expanded the repertoire of biological functions that microbial cells can incorporate into their physiological and metabolic agendas. Nowadays, designer cells can be constructed by adopting a combination of genome editing tools, chemical DNA synthesis and DNA assembly technologies—thereby fulfilling the practical goal of synthetic biology, that is, the construction of living cells from individual parts, which are purposefully assembled to yield a functional entity. As used herein, a biological chassis can be defined as the physical, metabolic and regulatory containment for plugging-in and plugging-out dedicated genetic circuits and regulatory devices. The integration of synthetic biology tools and strategies into advanced metabolic engineering has enabled the incorporation of a number of non-traditional microorganisms as hosts for developing efficient microbial cell factories. The (already extensive) list of the microbial hosts that can be adopted for such purposes continues to expand as more tools for precise gene and genome manipulation become available. Bacterial hosts traditionally employed in the production of useful products include *Escherichia coli, Bacillus subtilis, Streptomyces* sp., *Pseudomonas putida*, and *Corynebacterium glutamicum*, and for each there exists extensive background fundamental knowledge. In addition to these bacterial hosts, the present invention also includes the use of alternative hosts, some of which have been modified, such as via CRISPR systems. Building on the knowledge gained from the most used Gram-negative bacterial chassis, *E. coli*, and the Gram-positive bacterium *Bacillus subtilis*, the selection of other bacterial hosts for particular treatments of diseases will be readily determined by those of skill in the art due to the physical and genetic makeup and unique physiological and metabolic properties of microorganisms that are involved in specific diseases or conditions.

In the field of insect microbiomes, and in particular the gut microbiome of the honey bee, it is known that honeybees with compromised gut flora are malnourished and susceptible to infection. It is further acknowledged that as an herbicide, glyphosate works by blocking an enzyme called EPSP synthase in plants and microbes needed to create aromatic amino acids like phenylalanine and tryptophan. Glyphosate doesn't kill microbes, but it keeps them from growing, and most bacteria found in the gut of honey bees carry the gene for the enzyme. While some species of bacteria in the gut of honeybees are susceptible to glyphosate, others are less so because they carry a gene for a glyphosate-resistant version of EPSPS.

In certain embodiments of the present invention, the gut microbiome of the honeybee is manipulated so that it is able to at least partially degrade particular pesticides. In several embodiments, that pesticide is a neonicotinoid. In others, it is the pesticide fipronil. It is believed that certain pesticides are more rapidly eliminated from the honeybee gut than others. For example, it is believed that fipronil is bioaccumulated by honeybees more than neonicotinoids. Thus, over a prolonged exposure, fipronil becomes more lethal to honeybees than noenicitinoid pesticides. Mass mortalities of honey bees occurred in France in the 1990s coincident with the introduction of two agricultural insecticides, imidacloprid and fipronil. Employment of the present invention to inoculate the gut microbiomes of honeybees with bacteria engineered to degrade either or both a noenicitinoid or fipronil forms the basis of various embodiments of the present invention. Similarly, as it is believed that the effects of fipronil on bats and monarch butterflies, as well as other insects that one may wish to protect from the effects of fipronil, the discussion herein with respect to honey bees should be understood to be as applicable to these other creatures. The particular gut microbiomes of any particular creature are distinct, and as such one of skill in the art will appreciate that employing natively present microorganisms from any particular creature, such as a bat, monarch butterfly, etc. should be assessed and modifications to such creatures microbiome (e.g. gut, skin, oral, etc.) should be the focus to address carrying out fipronil degradation. For example, the particular bacteria in the microbiomes of particular creatures can be manipulated and modified so as to express fipronil degradation genes in a manner that will not significantly harm the creature, but will degrade amounts of fipronil such that the creature will not die. One of skill in the art will appreciate the various microbes that can be modified, e.g. through CRISPR systems as described herein to accomplish desired rates and degrees of fipronil degradation.

In certain embodiments, a method for providing a honey bee with the ability to assimilate pesticides involves inoculating a honey bee with a culture of pesticide degrading bacteria selected from the group consisting of *L. rhamnosus* and *L. plantarum*, whether or not purposefully manipulated (via CRISPR systems) to include genes whose expression by the pesticide degrading bacteria results in the degradation of the pesticide, said pesticide degrading bacteria being modified to include such genes via the use of a clustered regularly interspaced short palindromic repeats (CRISPR) CRISPR associated protein (Cas) system or using a clustered regularly interspaced short palindromic repeats (CRISPR) from *Prevotella* and *Francisella* 1 (Cpf1) nuclease.

One will appreciate that this Summary of the Invention is not intended to be all encompassing one of skill in the art will appreciate that the entire disclosure, as well as the incorporated references, provides a basis for the scope of the present invention as it may be claimed now and in future applications.

BRIEF DESCRIPTION OF THE FIGURES

FIG. 1 is a depiction of a honeybee, one of the major pollinators that is assisted by employing the method and system of the present invention.

FIG. 2 is a depiction of a Monarch butterfly, which is also a pollinator that is assisted by employing the method and system of the present invention.

FIG. 3 is a depiction of a bat, which is yet another pollinator that is assisted by employing the method and system of the present invention.

DETAILED DESCRIPTION OF PREFERRED EMBODIMENTS OF THE PRESENT INVENTION

Impacts to honey bees from sublethal exposure to imidacloprid in the presence of other stressors have been evaluated in laboratory studies and suggest that pesticides, such as imidacloprid, in combination with pathogens may impact colony health and immune function in honey bees. It is believed that several neonicotinoid insecticides are implicated in the decline of honey bee populations, including the following: imidacloprid. clothianidin, thiamethoxam, and dinotefuran.

To provide necessary and sufficient written disclosure and enablement of the various embodiments of the present invention, the following references are incorporated by reference in their entireties: 20110269119 to Hutchinson, et al.; 20130064796 to Hamdi; 20140212520 to Del Vecchio, et al.; U.S. Pat. No. 9,017,718 to Tan; 20140065218 to Lang et al.; U.S. Pat. Nos. 6,599,883; 8,383,201; 5,158,789; 20070218114 to Sorousch; 20040136923 to Davidson; U.S. Pat. No. 8,999,372 to Davidson; 20090196907 to Bunick; 20090196908 to Lee; 20030124178 to Haley; 20070293587 to Haley; 20100285098 to Haley; 2006-0204591 to Burrell; U.S. Pat. No. 7,087,249 to Burrelll; U.S. Pat. No. 6,210,699 to Acharya; U.S. Pat. No. 8,865,211 to Tzannis; 20140199266 to Park; U.S. Pat. No. 6,599,883 to Romeo; PCT/US2008/080362 to Dussia; 2007-0218114 to Duggan; 2004-0136923 to Davidson; 20110142942 to Schobel; 20040120991 to Gardner et al.; Fuchs et al. U.S. Pat. No. 4,136,162; 20040136923 to Davidson; U.S. Pat. No. 4,163,777 to Mitra; U.S. Pat. No. 5,002,970 to Eby, III; 20040096569 to Barkalow et al.; 20060035008 to Virgallito et al.; 20030031737 to Rosenbloom; U.S. Pat. No. 6,919,373 to Lam et al.; 20050196358 to Georglades et al.; U.S. Pat. No. 3,832,460 to Kosti; 2002002057 to Battey et al.; 20040228804 to Jones, et al.; U.S. Pat. No. 6,054,143 to Jones; U.S. Pat. No. 5,719,196 to Uhari; 20150150792 to Klingman; 20140333003 to Allen; 20140271867 to Myers; 20140356460 to Lutin; 20150038594 to Borges; U.S. Pat. No. 6,139,861 to Friedman; 20150216917 to Jones; 20150361436 to Hitchcock; 20150353901 to Liu; U.S. Pat. No. 9,131,884 to Holmes; 20150064138 to Lu; 20150093473 to Barrangou; 20120027786 to Gupta; 20150166641 to Goodman; 20150352023 to Berg; 20150064138 to Lu; 20150329875 to Gregory; 20150329555 to Liras; 20140199281 to Henn; US20050100559 (proctor and Gamble); 20120142548 to Corsi et al.; U.S. Pat. Nos. 6,287,610, 6,569,474, US20020009520, US20030206995, US20070054008; and U.S. Pat. No. 8,349,313 to Smith; and U.S. Pat. No. 9,011,834 to McKenzie; 20080267933 to Ohlson et al.; 20120058094 to Blasser et al.; 8716327 to Zhao; 20110217368 to Prakash et al.; 20140044734 to Sverdlov et al.; 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849; 20160348120 to Esvelt, et al., WO 2013026000 to Bryan and 20180020678 to Scharf et al. and Genomic signatures of honey bee association in an acetic acid symbiont, Smith et. al., bioRxiv preprint (Jul. 11, 2018).

It is believed that honey bees are highly dependent on their hive-mates for acquisition of their normal gut bacteria. Each worker acquires a fully expanded, typical gut community before it leaves the hive. Different colonies may maintain distinct community profiles at the strain level and thus, biological variation among colonies results in part from variation in gut communities. Worker bees develop a characteristic core microbiota within hives. Some Gram-positive members of the core microbiota can be acquired through contact with hive surfaces. Gram-negative species, S. alvi, G. apicola, and F. perrara, appear to be acquired through contact with nurse bees or with fresh feces but not through oral trophallaxis. The eusocial honey bees and bumble bees harbor two specialized gut symbionts, Snodgrassella alvi and Gilliamella apicola, and these microorganisms are specific to bees, with different strains of these bacteria assorting to host species.

Workers initially lack gut bacteria and gain large characteristic communities in the ileum and rectum within 4 to 6 days within hives. The core species of Gram-negative bacteria, Snodgrassella alvi, Gilliamella apicola, and Frischella perrara, are believed to be conveyed via nurses or hindgut material, whereas some Gram-positive species are often transferred through exposure to hive components. G. apicola and S. alvi are mutualistic symbionts with roles in both pathogen defense and nutrition. Their highly restricted distribution and phylogenetic correlation with their hosts are suggestive of a lengthy coevolutionary history with bees and with each other.

Workers possess a consistent set of nine bacterial species that are observed in bees collected worldwide and that dominate their gut communities. Members of the core gut community include Snodgrassella alvi (Betaproteobacteria: Neisseriales) and Gilliamella apicola and Frischella perrara (Gammaproteobacteria: Orbales); three species of Alphaproteobacteria ("Alpha-1," "Alpha-2.1," and "Alpha-2.2" and three Gram-positive species ("Bifido," corresponding to Bifidobacterium asteroides and "Firm-4" and "Firm-5" [both Firmicutes: Lactobacillaceae]. Discrete communities are found in different gut compartments: the crop and midgut contain very few bacteria, whereas hindgut compartments (ileum and rectum) house large communities with characteristic compositional profiles.

Interestingly, queen gut microbiomes do not always reflect those of the workers who tend to them and often lack many of the bacteria that are considered to be "core" to workers. Worker gut microbiotas are relatively consistent across unrelated colony populations and the microbiotas of the related queens are highly variable. Queen bee microbiomes are dominated by enteric bacteria in early life but are comprised primarily of α-proteobacteria at maturity. Bacterial communities in mature queen guts were similar in size to those of mature workers and were characterized by dominant and specific α-proteobacterial strains known to be associated with worker hypopharyngeal glands. It is believed that queen guts are colonized by bacteria from workers' glands.

Workers emerge from the pupal stage without the core gut bacteria and are fully colonized within several days postemergence. Early culture-based studies noted that bees removed from frames as pupae could remain free of gut bacteria through adulthood. During the pupal stage, the shedding of the integument and gut intima bars the carriage of gut microbes from the larval stage to the adult stage. Newly emerged A. mellifera workers (NEWs) are fed via oral trophallaxis by attendant nurse workers, consume bee bread, the fermented pollen food source stored within hives, and have many encounters with adult bees within the hive. Interactions with older bees as well as contact with the comb and bee bread are all potential inoculation routes for young workers.

Honey bees (Apis spp.) and bumble bees (Bombus spp) possess a distinctive gut microbiota dominated by three groups, S. alvi, G. apicola, and Lactobacillus spp., and these form the majority of the gut community. From an evolutionary perspective, specialized gut bacteria represent a unique but ubiquitous form of symbiosis that has thus far escaped close scientific scrutiny. For the eusocial corbiculate bees, there appear to be at least 4 lineages of gut bacteria exhibiting host specificity: S. alvi, G. apicola, Lactobacillus spp, and *Bifidobacterium* spp. *Gilliamella apicola* and *Snodgrassella alvi* are dominant members of the honey bee (*Apis* spp.) and bumble bee (*Bombus* spp.) gut microbiota.

Both *G. apicola* and *S. alvi* have relatively small genomes with reduced functional capabilities, which is consistent with their being specialized gut symbionts. *S. alvi* has lost the ability to use carbohydrates for carbon or energy: The glycolysis (Embden-Meyerhof-Parnas), pentose phosphate, and Entner-Doudoroff pathways needed to convert sugars to pyruvate are all missing key enzymes, and thus are predicted to be nonfunctional. This is surprising, considering that the bee diet consists mainly of carbohydrates. Instead, *S. alvi* possesses transporters for uptake of carboxylates, such as citrate, malate, α-ketoglutarate, and lactate. These can be used directly in the tricarboxylic acid cycle (TCA) cycle or, in the case of lactate, can be converted to pyruvate via lactate dehydrogenase. *S. alvi* is an obligate aerobe possessing NADH dehydrogenase and cytochrome bo and bd oxidases, but it lacks the TCA cycle enzyme succinyl-CoA synthetase, which catalyzes the interconversion of succinyl-CoA and succinate.

In particular embodiments, the present invention is directed to a system and method used for the biological control of the welfare of bees, and for prophylaxis and treatment of pathological disorders of bees caused by insecticides, and especially neonicotinoids. In certain embodiments, bacteria are modified, preferably via the CRISPR-Cas system, and such bacteria are then provided to honey bees in a fashion such that they can reside in the gut of the honey bee, such bacteria selected from the group consisting of: *S. alvi, G. apicola, Lactobacillus* spp, and *Bifidobacterium* spp. *Gilliamella apicola* and *Snodgrassella alvi*. The CRISPR-Cas system is employed to enable such modified species to degrade neonicotinoids. CRISPR elements, another widespread system of phage defense, are abundant in *G. apicola* genomes and may act synergistically with restriction modification systems.

In other embodiments, still other bacteria are introduced into a bee hive environment in a manner such that the bacteria are incorporated into the gut microbiota of at least worker bees or nurse bees, such that the colony can then acquire the ability to assimilate or degrade neonicotinoids that they are exposed to. In this regard, the following bacteria may be employed: *Lactobacillus paracasei* ssp., *Bifidobacterium bifidum, Lactobacillus acidophilus, Lactococcus lactis, Bifidobacterium animalis, Lactobacillus thermophilus*, and *Bacillus clausii; Lactobacillus plantarum* YML001, *Lactobacillus plantarum* YML004 and *Leuconostoc citreum* KM20; *Ochrobactrum intermedium* SCUEC4 strain, wherein the preservation number is CCTCC NO:M2014403; *Ochrobactrum intermedium* strain LMG3306. Particularly preferred microbes to employ, whether for extraction of their neonicotinoid genes for transplantation into the gut microbes of honey bees, or for the microbes inclusion as a microbe in the gut of honey bees, is a member of the genus *ochrobactrum*, in the alpha-2 subgroup of the domain Proteobacteria.

Other embodiments of the present invention are directed to modification of the bat gut microbiome so as to enhance the health and survival of bats, e.g. by providing bats with bacteria that can degrade neonicotinoids. In doing so, the adverse effects of WNS can be ameliorated. There are over 190 species within the Phyllostomidae, the New World leaf-nosed bat family. These bats are found from southern USA and northern Mexico to Argentina and are the most ecologically diverse family within the order Chiroptera. They show an evolutionary diversification of dietary strategies from insectivory to diets that include blood, meat from small vertebrates, nectar, fruit and complex omnivorous mixtures. Microbiomes of these bat species include: Gamma-, Alpha-, and Delta-proteobacteria, Tenericutes, Firmicutes, Bacteroidetes, Planctomycetes, Cyanobacteria; Proteobacteria; Gammaproteobacteria; *Enterobacteriales; Pasteurella;* Deltaproteobacteria; *Desulfurellales, Syntrophobacterales, Myxococcales; Rhodospirillales, Rhodobacterales, Rhizobiales, Rickettsiales; Firmicutes; Clostridia; Bacilli;* and Cyanobacteria. One striking difference in microbiome composition between plant—(fruit and nectar) vs. animal-eating bats (insectivores and sanguivores) is the great abundance of Crenarchaeota in the later. Overall, archaea are more abundant in the insect and blood eating bats.

The beneficial bacteria on the skin of bats provide vital functions, including processing of skin proteins, freeing fatty acids to reduce invasion of transient microorganisms, and inhibition of pathogenic microorganisms. While some probiotics have been contemplated in the biological control of disease in both aquaculture and agriculture, they have yet to be widely implemented in controlling wildlife disease.

In preferred embodiments of the present invention, bacteria that naturally occur in the bat microbiota are used and even more preferably, certain strains that have been modified to enhance their effectiveness and survival on a bat's skin or gut environment, and/or modified to have particular antibiotic characteristics, are employed. Those that are able to colonize the bat's skin and/or gut are preferred. Augmentation prior to *P. destructans* exposure is preferably used, but in other embodiments, bacterial augmentation even after exposure to *P. destructans* can be used to displace such pathogen.

One objective is to employ a strain of bacteria that can effectively persist on bat skin at high enough concentrations to limit *P. destructans* growth below levels that cause lethal disease.

In certain embodiments, the group of bacteria used comprise *Pseudomonas fluorescens*, which is known to produce a suite of antifungal compounds that can inhibit many plant fungal pathogens as well as the amphibian fungal pathogens, *Batrachochytrium dendrobatidis*. Some strains in the *P. fluorescens* group are also capable of producing mycolysing enzymes that can colonize the mycelia and conidia of fungi rendering them no longer viable. Thus, this bacteria, whether wild type or modified as described herein, is employed in various methods and systems as set forth herein as a biological control agent for reducing infection intensity and increasing survival of bats exposed to *P. destructans*.

Isolation of such antifungal bacteria can be obtained from the skin of bat species that appear to be better at surviving WNS, and thus, isolates from the skin of *E. fuscus*, which has lower mortality from WNS compared to other species, is preferably employed. In other embodiments, strains of *P. fluorescens* (PF3 and PF4) are used.

Administration of effective bacteria that can beneficially assist bats in combating the ill effects of neonicotinoids can be achieved in many ways, including but not limited to spraying colonies of bats with bacterial solutions; providing such bacterial solutions in places where bats frequent in a manner that they will be exposed to the same; purposeful capture and inoculation of members of a colony such that they will be able to then spread the bacteria to other bats in a colony, effectively inoculating the entire colony.

Certain aspects of the present invention are directed to employing genes from the microbe *Ochrobactrum intermedium* such that bats are able to assimilate and degrade neonicotinoids. Other embodiments employ inoculation of bats with a culture of neonicotinoid degrading bacteria, such as one or more of *Ochrobactrum intermedium*, *Agrobacterium tumefaciens* S33, *Apergillus oryzae*, *Pseudomonas putida* S16; *Arthrobacter nicotinovarans*, *Microsporum gypseum*, *Pellicularia filamentosa* JTS-208, *Pseudomonas* sp. 41; *Microsporum gypseum*; *Pseudomonas* ZUTSKD; *Aspergillus oryzae* 112822; and *Ochrobactrum intermedium* DN2. Preferably wherein the bacteria collection or culture comprises *Ochrobactrum intermedium*, collection number CGMCC NO. 8839 is used. The invention further provides applications of the *Ochrobactrum intermedium* to foster degradation of neonicotinoid insecticides by bats while the microbe exists in the gut or skin of the bats, the gut of honey bees and in butterflies.

CRISPR systems may be employed to insert desired genes into the above mentioned (as well as others) microbes that inhabit the bat gut or skin so as to degrade particular insecticides, including neonicotinoids. The bat microbiome enhances host functions, contributing to host health and fitness. One aspect of the present invention is directed to improving bat fitness by modifying the bat microbiome, thus engineering evolved microbiomes with specific effects on the host bat fitness. Thus, by employing host-mediated microbiome selection, one is able to select and modify microbial communities indirectly through the host, thus influencing the bat microbiome and positively affecting bat fitness. The methods that may be used to impose artificial selection on the bat microbiome include various techniques known to those of skill in the art, including CRISPR-Cas and Cpl1 systems. Thus, while particular cultures of particular microbes can be purposefully included into bat populations so as to inhabit their gut or skin microbiome, and by doing so, providing the bats with the ability to degrade neonicotinoids, other embodiments are directed to engineering a modification of the bat gut or skin microbes that do not already possess such neonicotinoid degradation genes.

In certain embodiments, xenobiotic detoxification is employed. In particular embodiments, the conversion of lipid-soluble substances to water-soluble, excretable metabolites is achieved. In a primary detoxification step, a toxin structure is enzymatically altered and rendered unable to interact with lipophilic target sites. Such functionalization is affected primarily by cytochrome P450 monooxygenases (P450) and carboxylesterases (CCE), although other enzymes, including flavin-dependent monooxygenases and cyclooxygenases may also be employed. Further reactions typically involve conjugation of products of the above referenced step to achieve detoxification for solubilization and transport. Glutathione-S-transferases (GST) are the principal enzymes used, although other enzymes may include glycosyltransferases, phosphotransferases, sulfotransferases, aminotransferases, and glycosidases. Nucleophilic compounds can be rendered hydrophilic by UDP-glycosyltransferases. The final stage of detoxification involves transport of conjugates out of cells for excretion. Among the proteins involved in this process are multidrug resistance proteins and other ATP-binding cassette transporters.

In particular embodiments, the present invention is directed to a system and method used for the biological control of the welfare of bats, and for prophylaxis and treatment of pathological disorders of bats caused by insecticides, and especially neonicotinoids. In certain embodiments, bacteria are modified, preferably via the CRISPR-Cas system, and such bacteria are then provided to bats in a fashion such that they can reside in the gut or skin of the bats, such bacteria selected from the group consisting of: Gamma-, Alpha-, and Delta-proteobacteria, Tenericutes, Firmicutes, Bacteroidetes, Planctomycetes, Cyanobacteria; Proteobacteria; Gammaproteobacteria; *Enterobacteriales; Pasteurella*; Deltaproteobacteria; *Desulfurellales, Syntrophobacterales, Myxococcales; Rhodospirillales, Rhodobacterales, Rhizobiales, Rickettsiales*; Firmicutes; *Clostridia; Bacilli*; and Cyanobacteria.

In other embodiments, still other bacteria are introduced into a bat colony environment in a manner such that the bacteria are incorporated into the gut and/or skin microbiota of at least some bats, which can then "infect" other bats with such bacteria, and in so doing, the colony of bats can then acquire the ability to assimilate or degrade neonicotinoids that it is exposed to. In this regard, the following bacteria may be employed: *Lactobacillus paracasei* ssp., *Bifidobacterium bifidum, Lactobacillus acidophilus, Lactococcus lactis, Bifidobacterium animalis, Lactobacillus thermophilus*, and *Bacillus clausii; Lactobacillus plantarum* YML001, *Lactobacillus plantarum* YML004 and *Leuconostoc citreum* KM20; *Ochrobactrum intermedium* SCUEC4 strain, wherein the preservation number is CCTCC NO:M2014403; *Ochrobactrum intermedium* strain LMG3306. Particularly preferred microbes to employ, whether for extraction of their neonicotinoid genes for transplantation into the gut and/or skin microbes of bats, or for the microbes inclusion as a microbe in the gut or skin of bats, is a member of the genus *ochrobactrum*, in the alpha-2 subgroup of the domain Proteobacteria.

While not bound by theory, it is believed that still other microbes may be employed in various embodiments of the present invention to address the objective of degrading neonicotinoid-like compounds, such bacteria showing an ability to degrade nicotine. The CRISPR-Cas system is employed to enable such modified species to degrade neonicotinoids. Thus, such system can be used to provide gut or skin bacteria that may grow on the bat skin or gut and can include genes that achieve desired degradation of neonicotinoids via the use of or presence of such genes in nicotine degrading organisms, such as *Agrobacterium tumefaciens* S33, *Apergillus oryzae, Pseudomonas putida* S16; *Arthrobacter nicotinovarans, Microsporum gypseum, Pellicularia filamentosa* JTS-208, *Pseudomonas* sp. 41; *Microsporum gypseum; Pseudomonas* ZUTSKD; *Aspergillus oryzae* 112822; and *Ochrobactrum intermedium* DN2.

Microbial symbionts are important for host organisms, and insects rely on the communities of microorganisms in their guts for several functions. Hosts have evolved a range of mechanisms to protect themselves against parasites that are a large threat to their fitness. These defenses can extend beyond intrinsic host immunity and incorporate aspects of the environment in which host and parasite interact. Monarch butterfly (*Danaus plexippus*) larvae actively consume milkweeds (*Asclepias* spp.) that contain secondary chemical compounds, named cardenolides, which reduce parasite infection and virulence.

*Commensalibacter* is a genus of acetic acid bacteria and 16S rRNA gene sequences related to the *Commensalibacter* genus have been recovered from the guts of *Drosophila* species, honey bees, and bumble bees, as well as from *Heliconius erato* butterflies. The type strain *Commensalibacter intestini* A911 was isolated from *Drosophila* intestines, and the genome sequence of a *Commensalibacter* symbiont isolated from a monarch butterfly has been reported. *Commensalibacter papalotli* strain MX01, was isolated from the intestines of an overwintering monarch butterfly. The 2,332,652-bp AT-biased genome of *C. papalotli* MX01 is the smallest genome for a member of the Acetobacteraceae.

In certain embodiments, *Commensalibacter* bacteria are modified to render them able to degrade neonicotinoid insecticides and such bacteria are then purposefully provided to the gut biome of monarch butterflies to enable the butterflies to degrade such pesticides, and thus survive and remain viable for reproduction. In a particular embodiment, the genes responsible for the ability to degrade neonicotinoids are derived from the *Ochrobactrum intermedium* SCUEC4 strain, wherein the preservation number is CCTCC NO:M2014403; and/or *Ochrobactrum intermedium* strain LMG3306.

CRISPR systems may be employed to insert desired genes into various bacteria that can survive in the gut of the monarch butterfly such that these microbes can degrade particular insecticides, including neonicotinoids.

One aspect of the present invention is directed to improving monarch butterfly fitness by modifying the monarch butterfly microbiome, either by incorporation of select species of bacteria into existing gut microbiomes of the monarch butterfly, or by incorporation of genetic elements into existing bacteria within a monarch butterfly's gut such that the modified microbe is able to degrade neonicotinoids. These engineered microbiomes are purposefully designed to have with specific beneficial effects on the host monarch butterfly fitness. Thus, by employing host-mediated microbiome selection, one is able to select and modify microbial communities indirectly through the host, thus influencing the monarch butterfly microbiome and positively affecting monarch butterfly fitness. The methods that may be used to impose artificial selection on the monarch butterfly microbiome include various techniques known to those of skill in the art, including CRISPR-Cas and Cpl1 systems. Thus, particular cultures of particular microbes can be purposefully included into monarch butterfly populations so as to inhabit their gut microbiome, and by doing so, provide the monarch butterflies with the ability to degrade neonicotinoids. Other embodiments are directed to engineering a modification of the monarch butterfly gut microbes that do not already possess such neonicotinoid degradation genes.

Detoxification gene inventory reduction may reflect an evolutionary history of consuming relatively chemically benign nectar and pollen. Thus, certain embodiments are directed to the development of predictable microbiome-based biocontrol strategies by providing the ability of monarch butterflies to degrade or otherwise assimilate insecticides or other chemical agents, including neonicotinoids. Such a novel biocontrol strategy can not only be used to suppress pathogens, but can also be effectively used to establish microbiomes in a desirable beneficial composition for particular purposes.

In certain embodiments, xenobiotic detoxification is employed to address the problems associated with monarch butterfly health. In particular embodiments, the conversion of lipid-soluble substances to water-soluble, excretable metabolites is achieved. In a primary detoxification step, a toxin structure is enzymatically altered and rendered unable to interact with lipophilic target sites. Such functionalization is affected primarily by cytochrome P450 monooxygenases (P450) and carboxylesterases (CCE), although other enzymes, including flavin-dependent monooxygenases and cyclooxygenases may also be employed. Further reactions typically involve conjugation of products of the above referenced step to achieve detoxification for solubilization and transport. Glutathione-S-transferases (GST) are the principal enzymes used, although other enzymes in insects may include glycosyltransferases, phosphotransferases, sulfotransferases, aminotransferases, and glycosidases. Nucleophilic compounds can be rendered hydrophilic by UDP-glycosyltransferases. The final stage of detoxification involves transport of conjugates out of cells for excretion. Among the proteins involved in this process are multidrug resistance proteins and other ATP-binding cassette transporters.

Any one or more of appropriate bacteria can be modified to express particular genes that have been shown (for example by its inclusion in the bacteria *Ochrobactrum intermedium*) to degrade neonicotinoids in a manner that preserves monarch butterfly health. One of skill in the art can address compatibility issues with respect to the use of such bacteria and can make modifications thereto to render it tolerable and viable in the gut microbiome of the monarch butterfly. Genetic modification of existing microbes in the monarch butterfly gut can also be performed to render such native bacteria able to produce agents effective in degrading neonicotinoids.

Impacts to monarch butterflies from sublethal exposure to neonicotinoids, such as imidacloprid, especially in the presence of other stressors, is believed to result in severe and significant dysfunctions within and have an adverse impact on monarch colony health and to the immune function in individual monarch butterflies. It is believed that several neonicotinoid insecticides are implicated in the decline of monarch butterfly populations, including the following: imidacloprid. clothianidin, thiamethoxam, and dinotefuran.

In particular embodiments, the present invention is directed to a system and method used for the biological control of the welfare of monarch butterflies, and for prophylaxis and treatment of pathological disorders of monarch butterflies caused by insecticides, and especially neonicotinoids. In certain embodiments, bacteria are modified, preferably via the CRISPR-Cas system, and such bacteria are then provided to monarch butterflies in a fashion such that they can reside in the gut of the monarch butterfly, such bacteria selected from the group consisting of one or more bacteria in six bacterial families: the Acetobacteraceae (*Alphaproteobacteria*), Moraxellaceae and Enterobacteriaceae (Gammaproteobacteria), Enterococcaceae and Streptococcaceae (Firmicutes), and an unclassified family in the Bacteroidetes phylum. In particular embodiments, the bacteria employed in the present invention include one or more of the following: *Commensalibacter*, and in particular *Commensalibacter intestini* A911 and *Commensalibacter papalotli* strain MX01; *Lactobacillus paracasei* ssp., *Bifidobacterium bifidum, Lactobacillus acidophilus, Lactococcus lactis, Bifidobacterium animalis, Lactobacillus thermophilus*, and *Bacillus clausii; Lactobacillus plantarum* YML001, *Lactobacillus plantarum* YML004 and *Leuconostoc citreum* KM20*; Ochrobactrum intermedium* SCUEC4 strain, wherein the preservation number is CCTCC NO:M2014403*; Ochrobactrum intermedium* strain LMG3306. Particularly preferred microbes to employ, whether for extraction of their neonicotinoid genes for transplantation into the gut microbes of monarch butterflies, or for the microbes inclusion as a microbe in the gut of monarch butterflies, is a member of the genus *ochrobactrum*, in the alpha-2 subgroup of the domain Proteobacteria.

Modifying the gut microbiota of monarch butterflies to provide them with the ability to consume chemically defended plants can thus be achieved by varying the monarch butterflies associated microbial communities. Different microbes may be differentially able to detoxify compounds toxic to the monarch or may be differentially resistant to the potential antimicrobial effects of some compounds.

In certain embodiments, the administration of effective bacteria that can beneficially assist monarch butterflies in combating the ill effects of neonicotinoids can be achieved in many ways, including but not limited to spraying colonies of butterflies or caterpillars that will emerge as butterflies with bacterial solutions; providing such bacterial solutions in places where monarch butterflies frequent in a manner that they will be exposed to the same, such as by having bacteria provide in sweetened solutions that monarch butterflies are drawn to; purposeful capture and inoculation of members of a colony such that they will be able to then spread the bacteria to other bats in a colony, effectively inoculating an entire colony of monarch butterflies.

As one of skill in the art of living will appreciate, the reason to preserve nature is not merely within the realm of science, as beauty and literature are rooted in those creatures who share this earth with us. The philosophers of the past recognized this fact. Nietzsche once said: "And to me also, who appreciate life, the butterflies, and soap-bubbles, and whatever is like them amongst us, seem most to enjoy happiness." Our treasure lies in the beehive of our knowledge. We are perpetually on the way thither, being by nature winged insects and honey gatherers of the mind." Aristotle chimed in: "As the eyes of bats are to the blaze of day, so is the reason in our soul to the things which are by nature most evident of all." Karl von Frisch said "Nature has unlimited time in which to travel along tortuous paths to an unknown destination. The mind of man is too feeble to discern whence or whither the path runs and has to be content if it can discern only portions of the track, however small." So as Nabokov suggested, "do what only a true artist can do . . . pounce upon the forgotten butterfly of revelation." "Literature and butterflies are the two sweetest passions known to man."

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception, upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method for providing a honey bee with the ability to assimilate pesticides, comprising, inoculating a honey bee with a culture of pesticide degrading bacteria, wherein the pesticide degrading bacteria include genes whose expression by the pesticide degrading bacteria results in the degradation of the pesticide, said pesticide degrading bacteria being modified to include said genes using a clustered regularly interspaced short palindromic repeats (CRISPR) CRISPR associated protein (Cas) system or using a clustered regularly interspaced short palindromic repeats (CRISPR) from *Prevotella* and *Francisella* 1 (Cpf1) nuclease, said pesticide degrading bacteria selected from the group consisting of *L. rhamnosus* and *L. plantarum*.

2. The method as set forth in claim 1, wherein said genes express cytochrome P450 enzymes.

3. The method as set forth in claim 1, wherein said genes comprise P450 genes of the CYP6 and CYP3 Glade.

4. The method as set forth in claim 1, wherein said inoculating comprises spraying a honey bee with said pesticide degrading bacteria.

5. The method as set forth in claim 1, wherein said inoculating comprises providing the pesticide degrading bacteria in a sweetened solution.

6. The method as set forth in claim 1, wherein the pesticide comprises a neonicotinoid insecticide.

7. The method as set forth in claim 1, further comprising employing a different CRISPR-Cas9/CRISPR-Cpf1 to ameliorate pathogens in the honey bee gut.

8. The method as set forth in claim 1, wherein said inoculating comprises providing the pesticide degrading bacteria in a sweetened solution or spraying a honey bee with said pesticide degrading bacteria.

9. The method as set forth in claim 6, wherein said genes express cytochrome P450 enzymes.

10. The method as set forth in claim 1, further comprising employing CRISPR-Cas9/CRISPR-Cpf1 to delete antibiotic resistance genes transferred to pathogenic bacteria in the honey bee gut.

11. The method as set forth in claim 2, further comprising employing a different CRISPR-Cas9/CRISPR-Cpf1 to ameliorate pathogens in the honey bee gut.

12. A method for providing a honey bee with the ability to assimilate pesticides, comprising, providing a honey bee with a culture of pesticide degrading bacteria, wherein the pesticide degrading bacteria include genes whose expression by the pesticide degrading bacteria results in the degradation of the pesticide, wherein said step of providing comprises using bacteriophage as a delivery vehicle for said genes, and wherein said pesticide degrading bacteria comprises *L. rhamnosus*.

13. The method as set forth in claim 12, wherein said genes express cytochrome P450 enzymes.

14. The method as set forth in claim 12, wherein said genes comprise P450 genes of one of the CYP6 and CYP3 clades.

15. The method as set forth in claim 12, wherein said genes are selected from the group consisting of a CYP353D1v2 gene and a SCL3-10 nitrile hydratase beta subunit gene.

16. The method as set forth in claim 12, further comprising employing CRISPR-Cas9/CRISPR-Cpf1 to delete antibiotic resistance genes transferred to pathogenic bacteria in the honey bee gut.

17. The method as set forth in claim 12, further comprising improving honey bee fitness by modifying the honey bee microbiome by using CRISPR-Cas9/CRISPR-Cpf1 to select and modify microbial communities to positively affect honey bee fitness.

18. The method as set forth in claim 12, wherein the pesticide degrading bacteria further comprises bacteria selected from the group consisting of: *Lactobacillus* spp, *Bifidobacterium* sp., *Gilliamella apicola* and *Snodgrassella alvi*.

19. The method as set forth in claim 16, further comprising employing a different CRISPR-Cas9/CRISPR-Cpf1 to ameliorate pathogens in the honey bee gut.

* * * * *